United States Patent
Brady et al.

(10) Patent No.: US 6,878,127 B2
(45) Date of Patent: Apr. 12, 2005

(54) DEVICES, SYSTEMS, AND METHODS FOR REDUCING LEVELS OF PRO-INFLAMMATORY OR ANTI-INFLAMMATORY STIMULATORS OR MEDIATORS IN THE BLOOD

(75) Inventors: James A Brady, South Hampton, NY (US); James F Winchester, New York, NY (US); Vadim Davankov, Moscow (RU); Maria Tsyurupa, Moscow (RU); Ludmila Pavlova, Moscow (RU); Frank M Norris, New York, NY (US); Peter J Quartararo, Jr., New York, NY (US); Jamie A Salsberg, New York, NY (US)

(73) Assignee: RenalTech International, LLC, Mammouth Junction, NJ (US)

( * ) Notice: Subject to any disclaimer, the term of this patent is extended or adjusted under 35 U.S.C. 154(b) by 0 days.

(21) Appl. No.: 10/036,759

(22) Filed: Dec. 21, 2001

(65) Prior Publication Data

US 2002/0197251 A1 Dec. 26, 2002

Related U.S. Application Data

(63) Continuation-in-part of application No. 09/832,159, filed on Apr. 10, 2001, and a continuation-in-part of application No. 09/829,252, filed on Apr. 10, 2001, now abandoned.

(51) Int. Cl.[7] .......... A61K 37/00; A61K 39/00; A61K 39/395; C02F 1/00; B01D 27/00

(52) U.S. Cl. .......... 604/6.09; 604/6.16; 422/44; 424/140.1; 424/158.1; 210/767; 210/437

(58) Field of Search .......... 210/767, 263–64, 210/252–256, 282–83, 287–88, 294, 321.6, 322, 323.1–323.2, 348, 500.1, 502.1, 503–4, 506, 500.27–500.43; 424/155.1, 7.23, 400, 422–25, 450, 130.1, 140.1, 140.7, 148.1, 149.1, 158.1, 159.1, 520, 529–31; 435/6; 422/44; 500/380–81, 385–86, 388.23

(56) References Cited

U.S. PATENT DOCUMENTS

| 4,668,396 A | 5/1987 | Baurmeister et al. |
| 5,277,820 A | 1/1994 | Ash |
| 5,298,016 A | 3/1994 | Gordon |
| 5,407,581 A | 4/1995 | Onodera et al. |
| 5,437,861 A | 8/1995 | Okarma et al. |
| 5,523,096 A | 6/1996 | Okarma et al. |

(Continued)

OTHER PUBLICATIONS

"Microparticles for Hemoperfusion and Extracorporeal Therapy"; Mikhalovsky, S.; 1999; MML Series, vol. 2.

*Primary Examiner*—Patricia Bianco
(74) *Attorney, Agent, or Firm*—Ryan Kromholz & Manion, S.C.

(57) ABSTRACT

Devices, systems, and methods reduce levels of pro-inflammatory or anti-inflammatory stimulators or mediators in blood by selective adsorption. The devices, systems, and methods are useful in situations where abnormal levels of or unregulated or excessive interaction among pro-inflammatory or anti-inflammatory stimulators or mediators occur, or during events that do induce or have the potential for inducing abnormal production of pro-inflammatory or anti-inflammatory stimulators or mediators. The devices, systems, and methods serve to prevent, control, reduce, or alleviate the severity of the inflammatory response and disease states that are associated with abnormal levels of or unregulated or excessive interaction among pro-inflammatory or anti-inflammatory stimulators or mediators.

24 Claims, 10 Drawing Sheets

U.S. PATENT DOCUMENTS

| | | |
|---|---|---|
| 5,545,721 A | 8/1996 | Carroll et al. |
| 5,639,376 A | 6/1997 | Lee et al. |
| 5,726,156 A | 3/1998 | Girten et al. |
| 5,726,166 A | 3/1998 | Playfair et al. |
| 5,730,713 A | 3/1998 | Okarma et al. |
| 5,760,001 A | 6/1998 | Girten et al. |
| 5,760,177 A | 6/1998 | Iwanaga et al. |
| 5,773,384 A * | 6/1998 | Davankov et al. .......... 502/402 |
| 5,786,332 A | 7/1998 | Girten et al. |
| 5,902,877 A | 5/1999 | Hirai et al. |
| 5,904,663 A | 5/1999 | Braverman et al. |
| 5,912,327 A | 6/1999 | Li et al. |
| 5,919,369 A | 7/1999 | Ash |
| 6,030,615 A | 2/2000 | Bucala et al. |
| 6,037,458 A | 3/2000 | Hirai et al. |
| 6,039,946 A | 3/2000 | Strahilevitz |
| 6,087,300 A | 7/2000 | Davankov et al. |
| 6,114,466 A | 9/2000 | Davankov et al. |
| 6,127,311 A | 10/2000 | Davankov et al. |
| 6,132,610 A | 10/2000 | Hirai et al. |
| 6,133,393 A | 10/2000 | Davankov et al. |
| 6,136,424 A | 10/2000 | Davankov et al. |
| 6,153,707 A | 11/2000 | Davankov et al. |
| 6,156,851 A | 12/2000 | Davankov et al. |
| 6,159,377 A | 12/2000 | Davankov et al. |
| 6,203,997 B1 | 3/2001 | Romaschin et al. |
| 6,238,795 B1 | 5/2001 | Strom et al. |
| 6,245,738 B1 | 6/2001 | Suto et al. |
| 6,287,516 B1 | 9/2001 | Matson et al. |
| 6,337,368 B1 | 1/2002 | Kobayashi et al. |
| 6,365,147 B1 | 4/2002 | Luo et al. |
| 6,416,487 B1 | 7/2002 | Braverman et al. |
| 6,498,007 B1 | 12/2002 | Adachi et al. |
| 2003/0095256 A1 | 5/2003 | Cargill et al. |

* cited by examiner

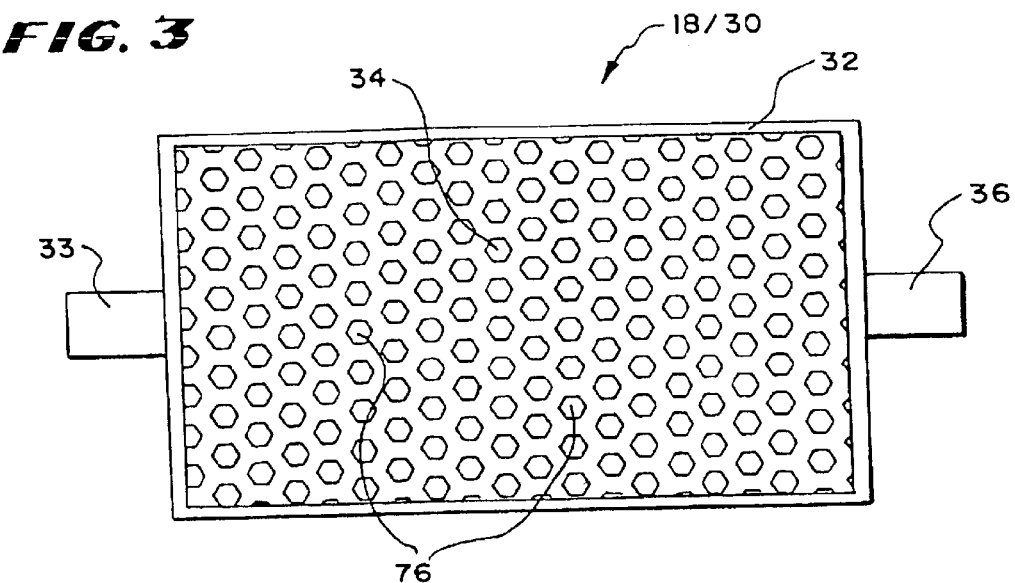
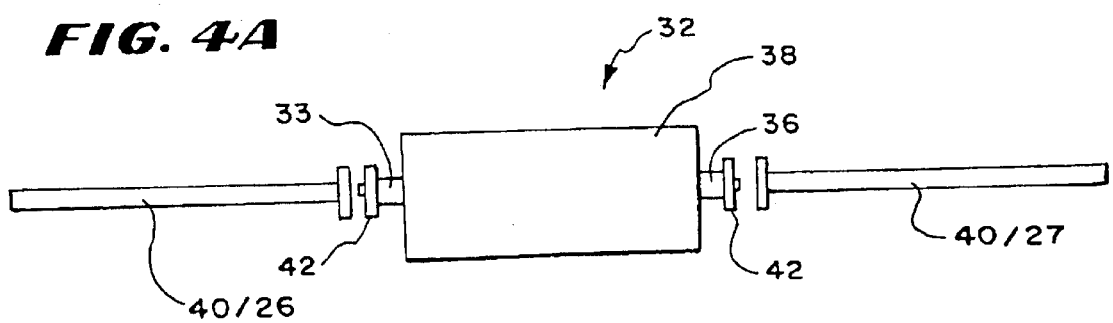
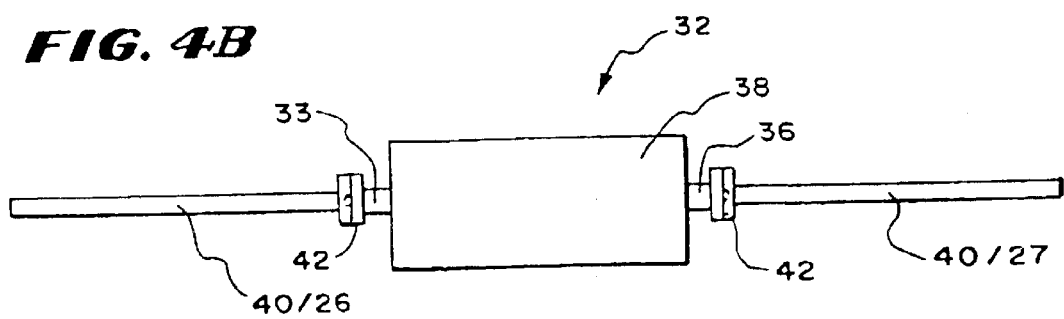

DEVICES, SYSTEMS, AND METHODS FOR REDUCING LEVELS OF PRO-INFLAMMATORY OR ANTI-INFLAMMATORY STIMULATORS OR MEDIATORS IN THE BLOOD

RELATED APPLICATIONS

This application is a continuation-in-part of co-pending U.S. patent application Ser. No. 09/832,159, filed Apr. 10, 2001, and entitled "System for Treating Patient with Bacterial Infections," which is incorporated herein by reference. This application is also a continuation-in-part of U.S. patent application Ser. No. 09/829,252, filed Apr. 10, 2001, now abandoned and entitled "Method of Treating Patient with Bacterial Infections," which is also incorporated herein by reference. This application claims, under 35 U.S.C §120, the benefit of the filing date of U.S. patent application Ser. No. 09/294,224, filed Apr. 19, 1999, and entitled "Method for Removing Beta-2 Microglobulin from Blood," (now U.S. Pat. No. 6,416,487) which is a continuation-in-part of U.S. patent application Ser. No. 08/902,727, filed Jul. 30, 1997 (now U.S. Pat. No. 5,904,663).

FIELD OF THE INVENTION

This invention relates to devices, systems, and methods for removing targeted proteins or toxins from the blood, blood products, or physiologic fluids.

BACKGROUND OF THE INVENTION

In animals, an inflammatory response occurs when tissues are injured by bacteria, trauma, toxins, heat, or other agents, which can be collectively referred to as "Inflammatory Agents." The nature and character of a given inflammatory response is regulated by the complex interaction of a variety of pro-inflammatory or anti-inflammatory stimulators or mediators, which are synthesized and released by tissue. Known species of pro-inflammatory or anti-inflammatory stimulators or mediators include, but are by no means limited to, cytokines, nitric oxide, thromboxanes, leukotrienes, platelet-activating factor, prostaglandins, kinins, complement factors, superantigens, monokines, chemokines, interferons, free radicals, proteases, arachidonic acid metabolites, prostacyclins, beta endorphins, myocardial depressant factors, anandamide, 2-arachidonoylglycerol, tetrahydrobiopterin, and chemicals including histamine, bradykinin, and serotonin. The discovery of new (i.e., previously unrecognized) species of pro-inflammatory or anti-inflammatory stimulators or mediators occurs almost daily.

The nature and intensity of inflammatory responses differ, depending on the site which has been invaded, and on the character of the Inflammatory Agent(s), and the interaction of pro-inflammatory or anti-inflammatory stimulators or mediators involved.

The inflammatory response, when regulated and localized, is beneficial. However, if not regulated and generalized, the inflammatory response can cause significant tissue injury and even death.

For example, cytokines are a class of proteins produced by macrophages, monocytes, and lymphocytes in response to viral or bacterial infection, as well as in response to T cell stimulation during an immune response. Cytokines are normally present in very low concentrations in the blood or tissues.

The structures and activities of cytokines have been the subject of many studies. It has become apparent that cytokines possess a wide spectrum of immunological and non-immunological activities. It is also apparent that cytokines affect diverse physiologic functions, such as cell growth, differentiation, homeostasis and pathological physiology. It is clear that cytokines have multiple biological activities and interact with more than one cell type. Cytokines are also known to be capable of stimulating their own synthesis, as well as the production of other cytokines from a variety of cell types. This phenomenon is called the "cytokine cascade."

Cytokine cascades are associated with systemic changes arising from infection and tissue injury and, in this context, they serve a myriad of biological functions. For example, various cytokines, categorized as the interleukins (IL), interferons (IF), and tumor necrosis factor (TNF), are produced during immune and inflammatory responses. These cytokines beneficially control various aspects of these responses. In this situation, the cytokine cascade mediates normal host defense responses, cell regulation, and cell differentiation.

However, it has been observed that the function of cytokine production can become disordered. This can lead to the presence of larger than normal concentrations of cytokines. When the cytokine cascade becomes disordered, there can be a rapid extension and amplification of the intended localized host response in such a way that only one or a few initiating stimuli trigger the eventual release and participation of scores of host mediators. Although a number of features of the host response assist in fighting off invasion, an overly robust or poorly modulated endogenous response can rapidly accelerate to produce other profound alterations in host homeostasis at the cellular, tissue, and systemic levels. As a result, cytokine expression in a region of the body where tissues or organs are legitimately subject to bacterial infection or an immune response challenge, can, when disordered, lead to unwanted destruction of healthy tissue elsewhere in the body. Larger than normal concentrations of certain cytokines can cause disease and other deleterious health effects, some of which can be lethal.

For example, a disordered cytokine cascade that leads to the increased presence of the cytokines IL-1 and TNF can, alone or in combination, cause a state in animals clinically identical to "septic" shock. It is recognized that septic shock arises due to the individual, combined, and concerted effects of a large number of cytokines. It is a condition inflicting more than 450,000 Americans every year. Cytokine-induced septic shock can be brought about by infection by a variety of microorganisms, including not only bacteria but also viruses, fungi, and parasites. Septic shock can also be initiated by host response to invasion in general, such as by cancer or as a result of major surgery or trauma. Septic shock is a potentially lethal cytokine-mediated clinical complication against which there is no generally effective therapeutic approach.

One of the best studied examples of cytokine-induced septic shock is the case of infection by gram-negative bacteria. It is believed that the appearance of bacterial endotoxins, such as lipopolysaccharide (LPS), in the host bloodstream leads to the endogenous production of a variety of host factors that directly and indirectly mediate the toxicity of LPS. These host-derived mediators include many now well-recognized inflammatory cytokines, as well as endocrine hormones, in addition to a number of other endogenous factors such as leukotrienes and platelet activating factor. Among the interacting factors that together comprise the cytokine cascade, the cytokine TNF alpha is believed to be the most important identified to date. During the ensuing cytokine cascade, the mediators that appear early in the invaded host are thought to trigger the release of later appearing factors. Many of the cytokine mediators not only exert direct functions at the targeted tissues, but also at other local and remote tissues, where subsequent responses to other mediators produced during the cascade occur, and so on. The result, if unchecked, can be a multifaceted pathological condition, which is characterized most prominently by deleterious hemodynamic changes and coagulopathy leading to multiple organ failure and, often, to death.

Multiple attempts have been made and still many others are currently underway to block specific mediators of this response. These attempts have been relatively unsuccessful. Therapy aimed at single mediators cannot effectively attenuate the entire response. Furthermore, it is the duration rather than the intensity of inflammation that correlates best with outcome, in that the longer the duration of over-expression of proinflammatory cytokines the higher the mortality. Systemic inflammation results in organ injury which results in the prolongation of the inflammatory response and thus, more organ injury.

Less lethal but just as profound physiologic effects can occur as a result of abnormal production of certain cytokines, without the presence of exogenous bacterial toxins. As one example, cytokine TNF-alpha has been found to be an anti-tumor cytokine. As a result, TNF-alpha has been expected to be useful as an antitumor agent. However, it has been discovered that TNF-alpha is identical with cachectin, which is a cachexia-inducing factor. The disordered production of TNF-alpha has also been correlated with, not only septic shock, but the incidence of rheumatoid arthritis, adult respiratory distress syndrome (ARDS), the severity of viral hepatitis, myocardial ischemia, and the inhibition of myocardial contraction. Also, TNF has recently been shown to be involved in initiating the expression of human immunodeficiency virus in human cells that carry latent virus, which could be a contributing factor in the expression of latent AIDS virus in certain individuals. Furthermore, a correlation between the TNF level in the blood and blood pressure has also been observed. As TNF levels increase, blood pressure decreases, which can lead to serious complications such as kidney failure.

It has also been observed that TNF-alpha also has an activity of stimulating production of other types of cytokines, such as IL-1, etc. It is known that the cytokine IL-1 is an important agent for inducing and transmitting the systemic biological response against infection and inflammation. IL-1 induces the usual, desirable responses observed in inflammation in general, such as fever, increase of leukocytes, activation of lymphocytes, induction of biosynthesis of acute phase protein in liver. It also known that this cytokine has a strong antitumor activity.

However, when IL-1 is produced in abnormally larger amounts, it may contribute to the severity of chronic inflammatory diseases, such as rheumatoid arthritis. Thus, the abnormal activation of various cytokines such as the interleukins (IL) and tumor necrosis factor (TNF) is believed responsible for the tissue damage and pain that occurs in various inflammatory conditions like rheumatoid arthritis. In rheumatoid arthritis, levels of TNF, IL-1, IL-6 and IL-8 increase dramatically and can be detected in the synovial fluid. The cytokine cascade induced by expression of these cytokines results in depressed lipoprotein metabolism as well as bone and cartilage destruction.

As another example, the cytokine IL-6 plays an important role in antibody production in B cells. The cytokine IL-6 also is an important factor in body systems, e.g., the hematopoietic system, nervous system, and the liver, as well as in immune system. For example, IL-6 is effective for inducing proliferation and differentiation of T cells, inducing the production of protein at acute phase by acting on hepatic cells, and promoting the growth of cells in bone marrow.

However, it has also been observed that there is a correlation between the abnormal secretion of IL-6 and various disease states, e.g., autoimmune diseases, such as hypergammaglobulinemia, chronic articular rheumatism, and systemic lupus erythematosus; the abnormal state of polyclonal B cells, as well as in the development of the abnormal state of monoclonal B cells such as myeloma cells; Castleman's disease accompanied with tumor of the lymph nodes, for which the cause is unknown; primary glomerular nephritis; and the growth of mesangial cells.

As yet another example, in bacterial infections, cytokines such as IL-8 act as a signal that attracts white blood cells such as neutrophils to the region of cytokine expression. In general, the release of enzymes and superoxide anions by neutrophils is essential for destroying the infecting bacteria. However, if cytokine expression causes neutrophils to invade, for example, the lungs, release of neutrophil enzymes and superoxide anion can result in the development of adult respiratory distress syndrome (ARDS), which can be lethal.

Despite their diverse and myriad functions, all cytokines share one common feature. They are all within a narrow size and molecular weight range of 8 to 28 kilodaltons. This size characteristic is extremely important for the clearance of cytokines from the blood. In this range, cytokines are effectively cleared by the liver and also the kidney, which clears all proteins below 50 kilodaltons in size. An imbalance between cytokine production and cytokine removal can cause damage to the liver and kidney.

In disease states where the kidney has failed—which is often the case in septic shock—hemodialysis or hemofiltration membranes are used as substitutes for the glomerular membrane of the kidney. However, artificial membranes are severely limited in their ability to clear cytokines from the blood due to their inadequate porosity. In fact, the predominant mechanism by which these membranes remove cytokines in clinical practice is not filtration, but rather nonspecific surface adsorption (J. Am Soc Nephrol 1999 April; 10(4): 846–53, Cytokine removal during continuous hemofiltration in septic patients, De Vriese A S, Colardyn F A, Philippe J J, Vanholder R C, De Sutter J H, Lameire N H). Typically these membranes have 0.5 to 2 square meters of surface area available for adsorption that becomes saturated within the first 30 to 90 minutes of treatment (Biomaterials September 1999; 20(17):1621–34, Adsorption of low molecular weight proteins to hemodialysis membranes: experimental results and simulations, Valette P, Thomas M, Dejardin P).

It is therefore clear that pro-inflammatory or anti-inflammatory stimulators or mediators, such as cytokines but by no means limited to cytokines, have the potential for both desirable physiologic results and undesirable physiologic results, depending upon the robustness and modulation of a particular inflammatory response. There is a need for straightforward and biocompatible devices, systems, and methods that serve to reduce or otherwise modulate levels of pro-inflammatory or anti-inflammatory stimulators or mediators in instances where abnormal levels of or unregulated or excessive interaction among such materials exist or can be expected to arise.

SUMMARY OF THE INVENTION

A detrimental inflammatory response, such as may occur, e.g., in the continuum from early sepsis to septic shock, or ischemia reperfusion, allograft rejection, chemical/biologic warfare casualties, has traditionally been viewed as a condition in which the local inflammatory response has become generalized and uncontrolled. Immune effector cells, especially neutrophils, possess potent cytotoxic capacity and when unchecked, this response can cause significant tissue injury.

However, while this traditional view is true, these intense inflammatory response conditions may also be viewed as a syndrome of immune suppression. Immune effector cells become dysfunctional and are no longer capable of normal immune surveillance. Such a condition results in increased susceptibility to recurrent infection, prolonged inflammation and continued tissue injury. This condition can be referred to as "immuno-paralysis" and can be easily demonstrated. When either intact septic animals or whole blood taken from septic patients is exposed to an inflammatory stimulus (e.g. endotoxin) the normal host response is severely inhibited.

From this perspective, therapy aimed at reducing an inflammatory response by targeting removal of some of the pro-inflammatory stimulus may not restore normal immune responsiveness and thus, may not improve outcome. Instead, a more desirable immune modulating strategy is to use a biocompatible adsorption medium to selectively adsorb a broader spectrum of pro-inflammatory or anti-inflammatory stimulators or mediators, which may include but is not neccesarily limited to cytokines, and to thereby restore immunologic stability, rather than indiscriminately inhibiting or stimulating one or another component. Such a strategy counters the immunologic instability of sepsis and other intense inflammatory response conditions by reducing the number, and thus the activity, of a wide array of both pro- and anti-inflammatory molecules. Such a strategy would "auto-regulate" itself, such that as one component of the response increased so too would the effect on that component. Finally, the desirable strategy might well be limited in its effect to the circulating pool of mediators rather than influencing the tissue levels where their activity may be beneficial.

The invention provides devices, systems, and methods for reducing levels of cytokines or other species of pro-inflammatory or anti-inflammatory stimulators or mediators in the blood, desirably whole blood, or blood products, or physiologic fluids in situations where abnormal levels of or unregulated or excessive interaction among such stimulators or mediators occur, or during events that do induce or have the potential for inducing abnormal production of or unregulated or excessive interaction among such stimulators or mediators. The devices, systems, and methods serve to prevent, control, reduce, modulate, or alleviate the severity of many physiologic conditions and disease states that are associated with abnormal levels of or unregulated or excessive interaction among pro-inflammatory or anti-inflammatory stimulators or mediators.

One aspect of the invention provides devices, systems, and methods for removing cytokines or other species of pro-inflammatory or anti-inflammatory stimulators or mediators from the blood, desirably whole blood, which are of use in acute situations where abnormal levels or unregulated or excessive interaction among such stimulators or mediators are present in individuals experiencing infection, or individuals experiencing an immune response. In such situations, the devices, systems and methods serve to modulate the inflammatory response by removing at least some of these stimulators or mediators from blood circulation, even as such stimulators or mediators are being produced by the individual to fight off the infection or invasion. This aspect of the invention serves to prevent an overly robust endogenous response, such as occurs, e.g., during septic shock. The devices, systems, and methods can be used alone or in combination with other forms of treatment targeted to the treatment of the bacterial infection and/or immune response.

Another aspect of the invention provides devices, systems, and methods for removing cytokines or other species of pro-inflammatory or anti-inflammatory stimulators or mediators from the blood, desirably whole blood, which are of use in situations where abnormal levels of or unregulated or excessive interaction among such stimulators or mediators are or may be present, or which involve events that do induce or have the potential for inducing abnormal production of or unregulated or excessive interaction among such stimulators or mediators in certain "at risk" individuals undergoing or about to undergo surgery, e.g., for treatment of burns or cardiac conditions; or for organ transplantation or reconstructive surgery, or other episodes involving ischemia-reperfusion injury. Other like situations, where abnormal levels of or unregulated or excessive interaction among such stimulators or mediators are or may be present, or which involve events that do induce or have the potential for inducing abnormal production of or unregulated or excessive interaction among such stimulators or mediators, include certain "at risk" individuals who have experienced trauma, such as burns, or "the crush syndrome." In such situations, the devices, systems, and methods serve to reduce the population of such stimulators or mediators by removing at least some of such stimulators or mediators from the blood circulation. This aspect of the invention also serves to modulate the inflammatory response by removing at least some pro-inflammatory or anti-inflammatory stimulators or mediators from the blood circulation, even as such stimulators or mediators are being produced by the individual in response to the surgery or trauma. This aspect of the invention serves to prevent an overly robust endogenous response, to prevent, e.g., septic shock or other conditions that may occur.

Another aspect of the invention provides devices, systems, and methods for removing cytokines or other species of pro-inflammatory or anti-inflammatory stimulators or mediators from the blood, desirably whole blood, which are of use in situations where abnormal cytokine levels are present in certain "at risk" individuals, whose chronic disease states are caused by or otherwise correlate with increased inflammatory activity. Such disease states include, e.g., rheumatoid arthritis; or lung disease such as emphysema or asthma; or pulmonary failure; or adult respiratory distress syndrome (ARDS); viral hepatitis; or myocardial ischemia; or autoimmune disease; AIDS; or as a result of accidental or intentional exposure to biological or chemical agents, such as anthrax. In such situations, the devices, systems, and methods serve to reduce the population of cytokines or or other species of pro-inflammatory or anti-inflammatory stimulators or mediators by removing such stimulators or mediators from the blood circulation. This aspect of the invention serves to treat a given disease condition by lessening the abnormal population of cytokines or other species of pro-inflammatory or anti-inflammatory stimulators or mediators, which is known or suspected of contributing to severity of the disease condition. The devices, systems and methods can be used alone or in combination with other treatment modalities for the disease condition.

Another aspect of the invention provides devices, systems, and methods for removing cytokines or other species of pro-inflammatory or anti-inflammatory stimulators or mediators from the blood, which are of use in other events that do induce or have the potential for inducing production of such stimulators or mediators due to extracorporeal blood processing, handling, or storage. These events can lead to an incidental or "obligatory" activation of the immune system due to subjecting the blood to extracorporeal treatment, pumping, or storage, e.g., for centrifugal or membrane blood separation; or for hemodialysis or hemofiltration; or for oxygenation. This obligatory activation of the immune system can activate production of cytokines or or other species of pro-inflammatory or anti-inflammatory stimulators or mediators in the blood as it undergoes extracorporeal treatment, handling, or storage. The increased presence of cytokines or other species of pro-inflammatory or anti-inflammatory stimulators or mediators in the treated, handled, or stored blood or blood product can, upon re-infusion, generate an incidental inflammatory response in the recipient's system, or at least can contribute to an incidental abnormal level of cytokines or other species of pro-inflammatory or anti-inflammatory stimulators or mediators in the recipient. In such events, the devices, systems and methods serve to reduce the population of cytokines or other species of pro-inflammatory or anti-inflammatory stimulators or mediators by removing such stimulators or mediators from the treated, handled, or stored blood or blood product. This aspect of the invention serves to prevent incidental inflammatory response conditions or disease states as a result of otherwise beneficial blood treatment, handling or storage, by lessening the population of cytokines or other species of pro-inflammatory or anti-inflammatory stimulators or mediators present in the re-infused blood or blood product.

The devices, systems, and methods that embody features of the invention also make it possible to restore a normal balance between pro-inflammatory stimulators or mediators and anti-inflammatory stimulators or mediators. For example, during a cytokine cascade, pro-inflammatory cytokines are typically generated in larger numbers in proportion to anti-inflammatory cytokines. In situations where abnormal cytokine levels exist, the removal of cytokines according to the invention will tend to remove more pro-inflammatory cytokines than anti-inflammatory cytokines, and thereby aid in maintaining a more normal balance between the two.

Another aspect of the invention provides devices, systems, and methods for removing cytokines or other species of pro-inflammatory or anti-inflammatory stimulators or mediators from physiologic fluids. For example, spent peritoneal dialysis solution can carry cytokines or other species of pro-inflammatory or anti-inflammatory stimulators or mediators. Systems and methods exist for regenerating spent peritoneal dialysis solution withdrawn from a patient, by removing waste and uremic toxins from the spent solution, as well as introducing electrolytes and buffering materials into the spent solution. In this way, fresh peritoneal dialysis solution can be recreated, obviating the need for bagged replacement solutions. In such situations, the devices, systems, and methods that embody this aspect of the invention remove cytokines or other species of pro-inflammatory or anti-inflammatory stimulators or mediators from the peritoneal dialysis solution, before, during, or after solution regeneration. This aspect of the invention serves to prevent incidental inflammatory response conditions or disease states as a result of exchange of spent peritoneal dialysis solution with regenerated peritoneal dialysis solution.

As another example, organs harvested for transplantation, e.g., kidney, liver, or heart, are typically stored for period of time in a suitable preservation solution until transplantation takes place. Storage of the organ in preservation solution can lead to the generation of cytokines or other species of pro-inflammatory or anti-inflammatory stimulators or mediators, which accumulate in the preservation solution. In such situations, the devices, systems, and methods that embody this aspect of the invention remove cytokines or other species of pro-inflammatory or anti-inflammatory stimulators or mediators from the preservation solution during organ storage and/or before transplantation of the organ occurs. In this way, the invention serves to prevent or at least ameliorate inflammatory response conditions or disease states as a result of organ transplantation.

As yet another example, body fluids that are removed from and then recycled back to the body during a given treatment modality can carry cytokines or other species of pro-inflammatory or anti-inflammatory stimulators or mediators, or cytokines or other species of pro-inflammatory or anti-inflammatory stimulators or mediators can be generated as a result of such treatment modalities. Treatment systems and methods exist for removing and recycling such fluids, e.g., lymphatic fluid, synovial fluid, spinal fluid, or cerebrospinal fluid. The devices, systems, and methods that embody this aspect of the invention can be used in association with such treatment modalities, to remove cytokines or other species of pro-inflammatory or anti-inflammatory stimulators or mediators from the body fluids before, during, or after primary treatment.

In preferred embodiments, the devices, systems, and methods remove cytokines or other species of pro-inflammatory or anti-inflammatory stimulators or mediators from the blood by selective adsorption. Desirably, the selective adsorption medium is characterized by a biocompatibility index that reflects a negligible production of cytokines or other species of pro-inflammatory or anti-inflammatory stimulators or mediators in the blood as a result of exposure to the medium. Thus, the adsorption medium, which beneficially serves to remove cytokines or other species of pro-inflammatory or anti-inflammatory stimulators or mediators from the blood, does not itself produce an offsetting result of generating additional cytokines or other species of pro-inflammatory or anti-inflammatory stimulators or mediators.

Other features and advantages of the inventions are set forth in the following specification and attached drawings.

BRIEF DESCRIPTION OF THE DRAWINGS

FIG. 3 is a side section view of a unitary, extracorporeal device containing an adsorption medium for removing cytokines or other species of pro-inflammatory or anti-inflammatory stimulators or mediators from the blood;

FIG. 4A is a side view of an exchangeable device that can be coupled to a conventional intravenous blood access catheter for the purpose of removing cytokines or other species of pro-inflammatory or anti-inflammatory stimulators or mediators from the blood;

FIG. 4B is a side view of the exchangeable device shown in FIG. 4A after being coupled to a conventional intravenous blood access catheter for the purpose of removing cytokines or other species of pro-inflammatory or anti-inflammatory stimulators or mediators from the blood;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

I. Systems and Methods for Removing Cytokines From the Blood

Cytokines and other species of pro-inflammatory or anti-inflammatory stimulators or mediators are low molecular weight proteins that are present in the blood. They are typically produced by the body in response to viral or bacterial infection and in response an immune response. Cytokines are also known to be capable of stimulating their own synthesis, as well as the production of other cytokines from a variety of cell types. Cytokines are normally present in very low concentrations in a tissue, but, due to an over-robust and unmodulated cytokine cascade or other causes, cytokines can be present in abnormal concentrations. In abnormal concentrations, cytokines can cause disease or septic shock.

As used in this Specification, the term "cytokine" as used herein is meant any secreted polypeptide that affects the functions of other cells, and is a molecule which modulates interactions between cells in the immune or inflammatory response. Cytokines are soluble protein and peptide humoral regulators. Type-1 cytokines are produced by Type-1 helper cells, e.g. IL2, IFN-gamma, IL12 and TNF-beta, and Type-2 cytokines are produced by Type-2 helper cells, e.g. IL4, IL5, IL6, IL10, and IL13. These may be pro-inflammatory or anti-inflammatory, chemotactic, paracrine, endocrine, juxtacrine, autocrine, and retrocrine. They also function as growth factors and apoptosis factors, involved in inflammation, septic shock, the systemic inflammatory response syndrome (SIRS), acute phase reactions, wound healing and neuroimmune networks. Others include IFN-alpha, -beta, -gamma, -omega, IL2-9, GCSF, MCSF, GMCSF, PGDF, IL-1-alpha, -beta, TNF-alpha, FGF, IL8, IP10, PF4, GRO, 9E3 and recombinant cytokines, muteins, and protein mimetics. Cytokines also comprise B-cell differentiation factors (BCDF), Bcell growth factors (BCGF), mitogenic cytokines, chemotactic cytokines (chemokines), colony stimulating factor (CSF), angiogenesis factors, t-cell replacing factor (TRF), heparin binding growth factor (HBGF), substance p (tachykinin), and kinins.

A. Acute or "At Risk" Conditions

Figure 1:
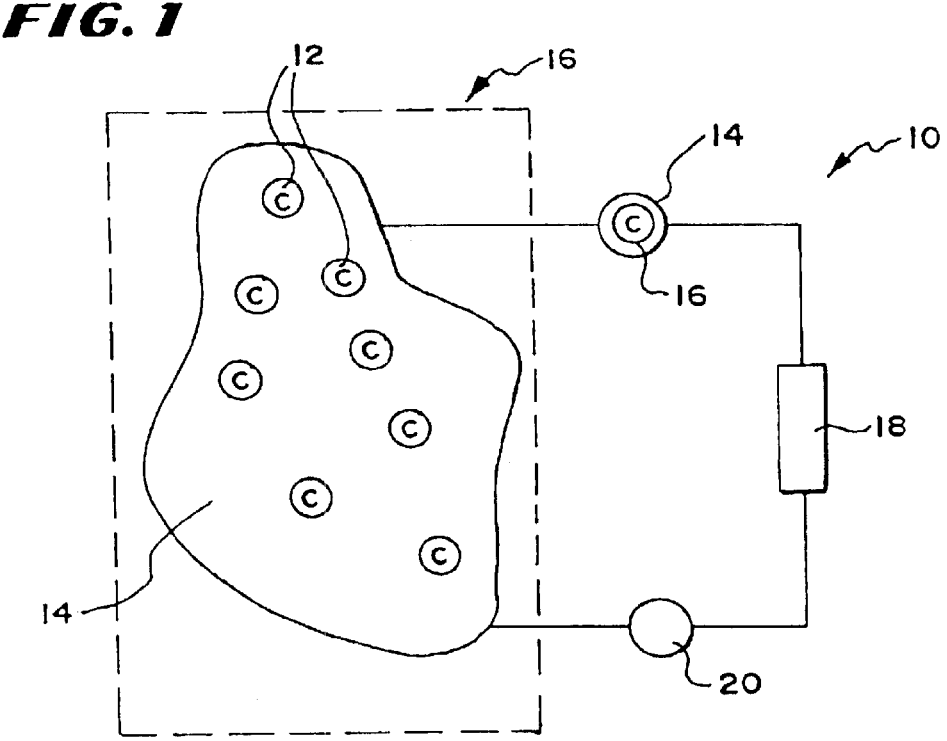
FIG. 1 is a schematic view of a system for removing cytokines or other species of pro-inflammatory or anti-inflammatory stimulators or mediators from the blood in acute or chronic or other "at risk" situations.

FIG. 1 generically shows a system 10 for removing cytokines 12 or other species of pro-inflammatory or anti-inflammatory stimulators or mediators (which are generally identified by circled C's in FIG. 1) from the blood 14, and desirably from whole blood. In the illustrated embodiment, the blood 14 emanates from a blood source 16. In the embodiment shown in FIG. 1, it is contemplated that the blood source 16 comprises the circulatory system of an individual.

In FIG. 1, it is also contemplated that the cytokines 12 or other species of pro-inflammatory or anti-inflammatory stimulators or mediators exist in the blood in abnormal levels, or at least the potential exists that the individual's levels of cytokines or other species of pro-inflammatory or anti-inflammatory stimulators or mediators may become abnormal, i.e., reach levels above normal physiologic levels, or otherwise create an unregulated or excessive inflammatory response interaction. Accordingly, as shown in FIG. 1, the system 10 includes a device 18 through which the blood 14 is circulated from the source 16 for the purpose of removing at least a portion of the population of cytokines 12 or other species of pro-inflammatory or anti-inflammatory stimulators or mediators carried in the blood 14. The removal of cytokines 12 or other species of pro-inflammatory or anti-inflammatory stimulators or mediators from the blood 14 serves to control, reduce, or alleviate the severity of many physiologic conditions and disease states that are associated with abnormal cytokine levels or an unregulated or excessive inflammatory response. As shown in FIG. 1, the cytokine-depleted blood 20 is returned to the individual blood source 16.

The cytokines 12 or other species of pro-inflammatory or anti-inflammatory stimulators or mediators may be present or pose the potential to exist in the blood 14 in abnormal levels for various reasons. For example, the individual may be in an acute condition, experiencing infection or an immune response. In this situation, cytokines 12 or other species of pro-inflammatory or anti-inflammatory stimulators or mediators are being generated by the individual to fight the infection or invasion. The concurrent removal of cytokines 12 or other species of pro-inflammatory or anti-inflammatory stimulators or mediators by the device 18 modulates the inflammatory response, e.g., to prevent the onset of a condition on a continuum from sepsis to septic shock or damage to tissue elsewhere in the body. Alternatively, the individual may be experiencing a condition on a continuum from sepsis to septic shock. In this situation, the concurrent removal of cytokines 12 or other species of pro-inflammatory or anti-inflammatory stimulators or mediators by the device 18 modulates the inflammatory response to terminate the deleterious hemodynamic changes and coagulopathy occasioned by septic shock, to prevent organ failure and death. In either situation, one prevention and the other treatment, the removal of cytokines 12 or other species of pro-inflammatory or anti-inflammatory stimulators or mediators by the device 18 aims to prevent an overly robust and possible lethal endogenous response.

The device 18 can be used alone or in combination with other forms of treatment targeted to the treatment of the bacterial infection and/or immune response and/or septic shock. Examples of other forms of treatment that can be used in combination with the device 18 include antibiotics, antimicrobial agents, antifungal agents, antiviral agents, and specific compounds such as activated protein-C.

In another embodiment, the cytokines 12 or other species of pro-inflammatory or anti-inflammatory stimulators or mediators may be present in abnormal levels because the individual possesses an "at risk" acute or chronic disease state, which is caused by or otherwise correlate with increased physiologic cytokine activity or an unregulated inflammatory response. Such disease states include, e.g., rheumatoid arthritis; or lung disease such as emphysema or asthma; or pulmonary failure; or adult respiratory distress syndrome (ARDS); viral hepatitis; or myocardial ischemia; or autoimmune disease; AIDS; or as a result of exposure to biological or chemical agents, such as anthrax. The removal of cytokines 12 or other species of pro-inflammatory or anti-inflammatory stimulators or mediators by the device 18 reduces the population of cytokines or other species of pro-inflammatory or anti-inflammatory stimulators or mediators to treat the severity of the disease condition. The treatment of the individual using the system 10 can be under acute conditions (due to the presence of severe symptoms). The treatment using the system 10 can also be under chronic conditions, as a part of scheduled, periodic treatment of the disease condition.

In either situation, the device 18 can be used alone or in combination with other treatment modalities beneficial for the disease condition. Examples of other forms of treatment that can be used in combination with the device 18 include antibiotics, antimicrobial agents, antifungal agents, antiviral agents, and specific compounds such as activated protein-C.

In another embodiment, the cytokines 12 or other species of pro-inflammatory or anti-inflammatory stimulators or mediators may be present in abnormal levels, or may potentially rise to abnormal levels, because the individual is "at risk" due to present or contemplated surgery, e.g., for treatment of burns or cardiac conditions; or for organ transplantation or reconstructive surgery, or other episodes involving ischemia-reperfusion injury. Alternatively, the individual can be "at risk" because of trauma, such as burns, or "the crush syndrome," which may or may not require corrective surgery. In such situations, cytokines 12 or other species of pro-inflammatory or anti-inflammatory stimulators or mediators have likely already been generated by the individual due to injury and trauma to the body, and resulting corrective surgery is likely to maintain or even increase generation of cytokines or other species of pro-inflammatory or anti-inflammatory stimulators or mediators. The removal of cytokines 12 or other species of pro-inflammatory or anti-inflammatory stimulators or mediators by the device 18, after the trauma and either before surgery, or during surgery, or after surgery, or a combination thereof, reduces the population of cytokines or other species of pro-inflammatory or anti-inflammatory stimulators or mediators to modulate the inflammatory response. The removal of cytokines 12 or other species of pro-inflammatory or anti-inflammatory stimulators or mediators by the device 18 aims to prevent an overly robust and possible lethal endogenous response, to prevent, e.g., septic shock or other unregulated or excessive inflammatory response conditions that may occur. The treatment using the system 10 can occur under acute conditions (i.e., as an adjunct to the surgical procedure or other treatment of the trauma), and/or under chronic conditions, as a part of a scheduled rehabilitation program following the trauma or surgery.

In either situation, the device 18 can be used alone or in combination with other treatment modalities beneficial for the injury and surgical procedure. Examples of other forms of treatment that can be used in combination with the device 18 include antibiotics, antimicrobial agents, antifungal agents, antiviral agents, and specific compounds such as activated protein-C.

B. Extracorporeal Blood Processing

Figure 2:
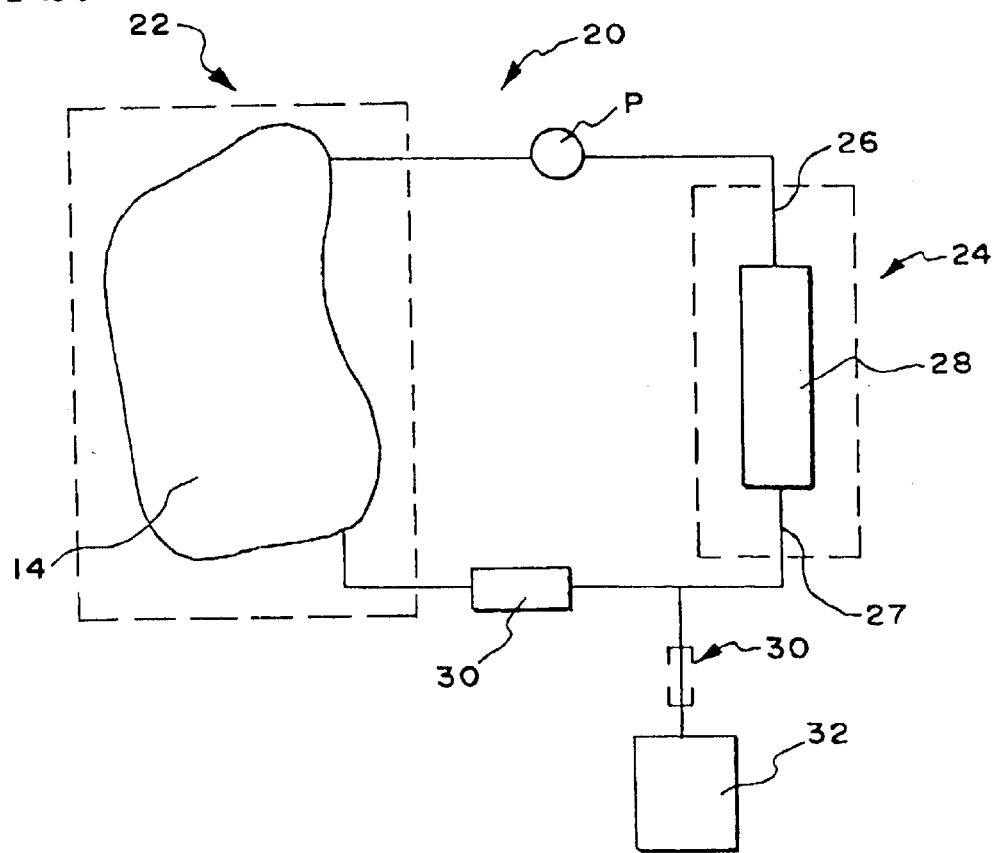
FIG. 2 is a schematic view of a system for removing cytokines or other species of pro-inflammatory or anti-inflammatory stimulators or mediators from the blood during an extracorporeal blood processing procedure, such as blood separation, dialysis, hemofiltration, or extracorporeal oxygenation.

FIG. 2 show a blood processing system 20 that removes cytokines 12 or other species of pro-inflammatory or anti-inflammatory stimulators or mediators from the blood 14 as it undergoes extracorporeal processing. In use, the system 20 is intended to convey the blood from a blood source 22 (typically, the circulatory system of a donor or patient) to an extracorpreal blood processing assembly 24. After processing, all or a portion of the blood is either returned to the circulatory system of the individual donor or patient, or retained for storage and subsequent transfusion to the same donor or patient, or to another recipient, or a combination thereof.

Typically, the functional components of the blood processing assembly 24 are a blood inlet line 26, a blood processor 28, and a blood outlet line 27. The blood from the donor or patient is conveyed by the blood inlet line 26 to the processor 28 for the desired processing. After processing, the blood is convey from the processor 28 by the blood outlet line 27. The system 20 may continuously or intermittently convey the blood to and from the blood processing assembly 24, typically using one or more peristaltic pumps (designated P in FIG. 2).

Depending upon the objectives of the processing, the blood outlet line 27 can be coupled directly to the donor or patient, so that the processed blood is returned directly to that individual. In other processing schemes, all or a portion of the processed blood is retained for storage and not returned to the donor or patient. In this arrangement, the blood outlet line 27 also communicates with a blood storage container 32.

The blood processing assembly 24 can be constructed in various ways and perform different processing functions.

1. Blood Separation

The blood processing assembly 24 can serve to separate whole blood into plasma and cellular blood components (i.e., blood products), typically, red blood cells and platelets. In this arrangement, the blood processing assembly 24 can comprise a centrifuge or a membrane that separates whole blood into its components. Depending upon the objectives of the device, all or some of the components are collected for storage and later transfusion. The components that are not collected are typically returned to the blood donor.

For example, in a process called plasmapheresis, plasma can be collected in an extracorpeal circuit for later fractionation to harvest therapeutic plasma proteins, e.g., Factor VIII. The remaining cellular components (red blood cells and platelets, along with the leukocytes) are returned to the blood donor.

Or, in a process called plasma exchange, plasma can be collected in an extracorpreal circuit. The plasma is discarded, and the cellular components (red blood cells, leukocytes, and platelets) are returned to the blood donor, along with a plasma-replacement fluid. Alternatively, the plasma itself can be treated by immunoadsorption, to remove undesired materials—e.g., antibodies—which is then returned with the cellular components to the individual.

As another example, in a process called plateletpheresis, the blood is circulated through an extracorpreal path through a centrifuge, which centrifugally separates and collects concentrated platelets for later transfusion. The remaining cellular components and plasma are returned to the donor. Alternatively, a volume of red blood cells or plasma, or both, can be retained for storage and later transfusion to recipients undergoing blood component therapy.

There are many other types of blood cell harvesting procedures in addition to plateletpheresis, where a targeted blood cell is collected, e.g., leukopheresis. There are also many other types of blood processing procedures in general, such as photopheresis (for inactivation of viral pathogens) or hypothermia, which circulate blood in extracorporeal paths to achieve desired therapeutic or diagnostic objectives.

The preceding examples process the blood on-line, that is, while the donor remains coupled to the system. In another arrangement, called manual collection, a unit of whole blood is drawn into a plastic blood collection bag, to which one or more plastic satellite bags are integrally connected. These arrangements of integrally connected bags are called multiple blood bag systems. After the unit of whole blood is drawn, the donor is disconnected. The whole blood is then subjected to off-line centrifugation while in the blood collection bag. The centrifugation separates the whole blood into layers of red blood cells and plasma, with an intermediate layer of leukocytes. The plasma can be either rich in platelets or poor in platelets, depending upon the centrifugal forces applied. The plasma component is transferred into a satellite bags, leaving the red blood cells (and leukocytes) behind in the blood collection bag. If rich in platelets, the plasma component can be further centrifugally separated in the satellite bag to obtain concentrated platelets. The components are stored in the individual plastic bags for later transfusion to recipients undergoing blood component therapy.

2. Hemodialysis or Hemofiltration

The blood processing assembly 24 can also carry out processes, called hemodialysis or hemofiltration, which emulate normal kidney activities for an individual whose renal function is impaired or lacking.

During hemodialysis, the blood from an individual is conveyed in an extracorporeal path along one side of a membrane. A dialysate is circulated on the other side of the membrane and forms a concentration differential across the membrane. Liquid and uremic toxins carried in the blood are drawn by the concentration differential across the membrane and out of the blood.

During hemofiltration, the blood from an individual is conveyed in an extracorporeal path along a semipermeable membrane, across which a pressure difference (called transmembrane pressure) exists. The pores of the membrane have a molecular weight cut-off that can pass liquid and uremic toxins carried in the blood.

In both hemodialysis and hemofiltration, the membrane pores do not pass formed cellular blood elements and plasma proteins. These components are retained and returned to the individual with the toxin-depleted blood, along with a replacement fluid. The replacement fluid restores, at least partially, a normal physiologic fluid and electrolytic balance to the blood. Hemodialysis and hemofiltration can be carried out as individual processes, or in combination.

A form of hemodialysis is also used to treat individuals suffering from jaundice caused by inadequate liver function or liver failure. In this indication, the blood carries abnormal levels of bilirubin, a breakdown product of hemoglobin normally removed by the liver. The blood is passed along one side of a dialysis membrane. Healthy liver cells are located on the opposite side of the membrane. The healthy liver cells remove bilirubin from the processed blood. In this treatment, the blood is passed before undergoing dialysis through an adsorption device (typically contained activated charcoal) to remove certain blood materials that are lethal to liver cells.

3. Oxygenation (Cardiopulmonary Bypass)

The blood processing assembly 24 can alternatively carry out a process called oxygenation. Oxygenation is carried out during cardiopulmonary bypass, during which the blood is circulated outside the heart and lungs while heart surgery occurs. During oxygenation, the blood conveyed from an individual is transported in an extracorporeal path along a membrane across which a oxygen concentration differential exists. Oxygen from the opposite side of the membrane is transported into the blood on the opposite side of the membrane, to emulate lung function.

4. Removal of Cytokines or Other Species of Pro-Inflammatory or Anti-Inflammatory Stimulators or Mediators Extracorporeal processing of the blood in the system 20 may trigger an incidental or "obligatory" activation of the components of the immune system carried by the blood. The sources of this incidental activation can include exposure to biomaterials in the inlet and return lines 26 and 28 or in the blood processing assembly 24 itself. External pumping of the blood can also trigger an incidental immune response. The centrifugal forces or shear forces developed by passage along a membrane can also trigger an incidental immune response.

The incidental activation of the immune system occasioned during blood processing can lead to the incidental generation of cytokines or other species of pro-inflammatory or anti-inflammatory stimulators or mediators. These cytokines or other species of pro-inflammatory or anti-inflammatory stimulators or mediators, to the extent that they are incidentally produced as a result of blood processing, will be transported by the blood that is returned to the donor or patient during processing, or by stored blood delivered to a recipient during transfusion. Entering the circulatory system of the donor or other recipient, these incidental cytokines or other species of pro-inflammatory or anti-inflammatory stimulators or mediators can serve to raise the levels of cytokines or other species of pro-inflammatory or anti-inflammatory stimulators or mediators in the donor or other recipient, and could lead to the generation of further cascades or inflammatory responses, during which further cytokines or other species of pro-inflammatory or anti-inflammatory stimulators or mediators and additional by-products of immune system activation are produced. Thus, processes that provide beneficial results in one respect can lead to incidental, potentially adverse results in another respect.

The blood processing system 20 therefore includes a device 30 that removes cytokines or other species of pro-inflammatory or anti-inflammatory stimulators or mediators from the processed blood.

In on-line blood processing systems—e.g., those systems in which the circulatory system of the donor or patient remains coupled to the processor 24 during processing—the device 30 can be coupled in-line either upstream or downstream of the processor 24 (in FIG. 2, the device 30 is shown positioned in the return line 28 for purposes of illustration). In this arrangement, cytokines or other species of pro-inflammatory or anti-inflammatory stimulators or mediators are removed during circulation of the blood through the extracorporeal circuit, thereby leading to reduced levels of cytokines or other species of pro-inflammatory or anti-inflammatory stimulators or mediators in the blood returned to the donor or patient.

In off-line blood processing systems—e.g., where the blood is processed after disconnecting the donor from the collection system—or in a system that collects a blood component for later transfusion to a recipient (as FIG. 2 shows)—it is desirable to place the device 30 either upstream of the blood component storage bag (as shown in phantom lines in FIG. 2)(so cytokines or other species of pro-inflammatory or anti-inflammatory stimulators or mediators are removed after blood processing and before storage of the blood component) or in a transfusion set coupled to the satellite blood component storage bag (so that cytokines or other species of pro-inflammatory or anti-inflammatory stimulators or mediators are removed during the act of transfusion of the processed blood component).

The device 30 serves to reduce the population of cytokines or other species of pro-inflammatory or anti-inflammatory stimulators or mediators by removing cytokines or other species of pro-inflammatory or anti-inflammatory stimulators or mediators from the treated, handled, or stored blood. The device 30 thereby serves to prevent incidental cytokine-induced or inflammatory response conditions or disease states as a result of otherwise beneficial blood treatment, handling or storage, by lessening the population of cytokines or other species of pro-inflammatory or anti-inflammatory stimulators or mediators present in the returned or re-infused blood. The removal by the device 30 of cytokines or other species of pro-inflammatory or anti-inflammatory stimulators or mediators generated as a result of extracorporeal blood processing aims to maintain a status quo condition in the immune system of the individual undergoing blood processing or the recipient of stored blood.

II. Devices for Removing Cytokines or Other Species of Pro-Inflammatory or Anti-Inflammatory Stimulators or Mediators From the Blood Cytokines and other species of pro-inflammatory or anti-inflammatory stimulators or mediators are low molecular weight, electrically neutral proteins, ranging in size from about 8000 to about 28,000 daltons. Cytokines or other species of pro-inflammatory or anti-inflammatory stimulators or mediators can be removed from the blood by various mechanism, e.g. by selective adsorption, or by ion exchange, or by non-specific adsorption to dialysis membranes. The devices 18 or 30 for removing cytokines or other species of pro-inflammatory or anti-inflammatory stimulators or mediators from the blood can therefore be variously constructed, depending upon the removal mechanism selected.

In the illustrated embodiment, selective removal by adsorption is the selected mechanism.

A. Unitary Extracorporeal Devices

Either device 18 or 30 can comprise a stand-alone, or unitary, extracorporeal component that can be coupled in-line to blood tubing at time of use.

In this arrangement (see FIG. 3), either device 18 or 30 desirably includes in its most basic form a housing 32. The housing 32 contains a medium 34 that removes cytokines or other species of pro-inflammatory or anti-inflammatory stimulators or mediators by adsorption.

The housing 32 includes an inlet 33 for conveying the blood into the housing 32 for contact with the adsorption medium 34. The housing 32 also includes an outlet 36 for conveying the blood from the housing after contact with the adsorption medium 34, during which all or a portion of the cytokines or other species of pro-inflammatory or anti-inflammatory stimulators or mediators present are removed.

Desired characteristics of the adsorption medium 34 will be described in greater detail later.

The transport of the blood through the adsorption medium 34 in the housing 32 can be accomplished in various ways, depending in large part upon the environment in which the device 18 or 30 is used. In the acute or chronic applications described, which involve use of the device 18, an external pump can be used to convey the blood through the housing 32 to remove cytokines or other species of pro-inflammatory or anti-inflammatory stimulators or mediators. Alternatively, blood tubing connected to the inlet 33 of the housing 32 can be coupled via a suitable blood access to an artery, while blood tubing connected to the outlet 36 of the housing 32 can be coupled by a suitable blood access to a vein, thereby using physiologic blood pressure to convey the blood through the housing 32 to remove cytokines or other species of pro-inflammatory or anti-inflammatory stimulators or mediators.

When used in association with a blood processing system, which involves use of the device 30, an external pump (identified as P in FIG. 2) is typically present to convey the blood through the blood processing assembly 24. In this arrangement, the external pump P that serves the blood processing assembly can concurrently provide the pressure to convey the blood through the housing 32 to remove cytokines or other species of pro-inflammatory or anti-inflammatory stimulators or mediators.

In an alternative embodiment shown in FIGS. 4A and 4B, the housing 32 can be configured to comprise an exchangeable component 38 that can be releasably coupled to a conventional intravenous blood access catheter 40, e.g., of the type widely used in intensive care units. The exchangeable component 38 provides particular ease of use in either acute or chronic indications, as above described, as individuals in such circumstances are typically already fitted with intravenous blood access catheters for other purposes. However, the exchangeable components 38 would also provide ease of use in the setting of extracorporeal blood processing, as the intravenous blood tubing comprising the blood inlet line 26 or blood outlet line 27 serving the processor 28 could be ready modified to include fittings to accommodate quick exchange of the component 38.

In this arrangement, the inlet 33 and 36 of the exchangeable component 38 and the catheter 40 (or inlet and outlet lines 26 and 27) would include, e.g., convention mating luer fittings 42, to enable quick attachment and removal in-line in the intravenous blood access catheter 40 or intravenous blood lines 26/27 serving the processor 28, as FIGS. 4A and 4B demonstrate.

Figure 5:
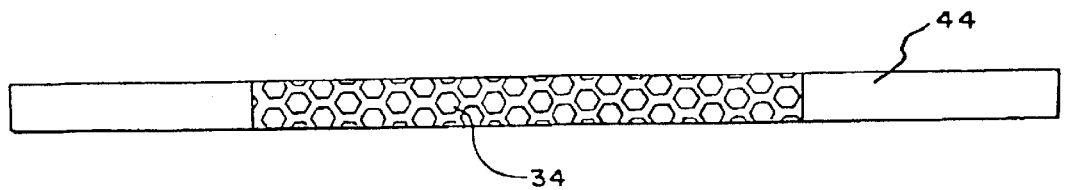
FIG. 5 is a side section view of an intravenous catheter having a wall that is impregnated with an adsorption material that removes cytokines or other species of pro-inflammatory or anti-inflammatory stimulators or mediators from the blood.
Figure 6:
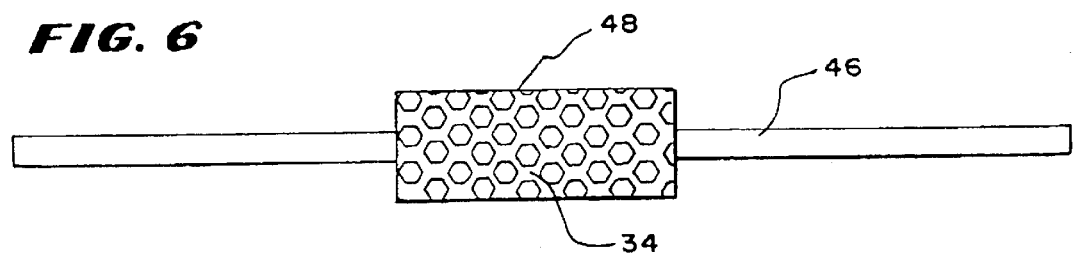
FIG. 6 is a side section view of an intravenous catheter having an integrally formed chamber containing an adsorption medium that removes cytokines or other species of pro-inflammatory or anti-inflammatory stimulators or mediators from the blood.

In another alternative embodiment shown in FIG. 5, all or a portion of the wall of an intravenous catheter 44 can be impregnated with the adsorption medium 34. In this arrangement, transport of the blood through the catheter 44 exposes the blood to the medium 34 for the removal of cytokines or other species of pro-inflammatory or anti-inflammatory stimulators or mediators. Alternatively (as shown in FIG. 6), an intravenous catheter 46 can include an integrally formed chamber 48 in which the adsorption medium 34 is housed. Thus, transport of the blood through the catheter 44 exposes the blood to the medium 34 for the removal of cytokines or other species of pro-inflammatory or anti-inflammatory stimulators or mediators. In the embodiments shown in FIGS. 5 and 6, the device 18 or 30 forms an integrated part of the blood transport path, so that a separate housing 32 per se is not required to contain the adsorption medium 34.

B. Ambulatory Applications

Figure 7:
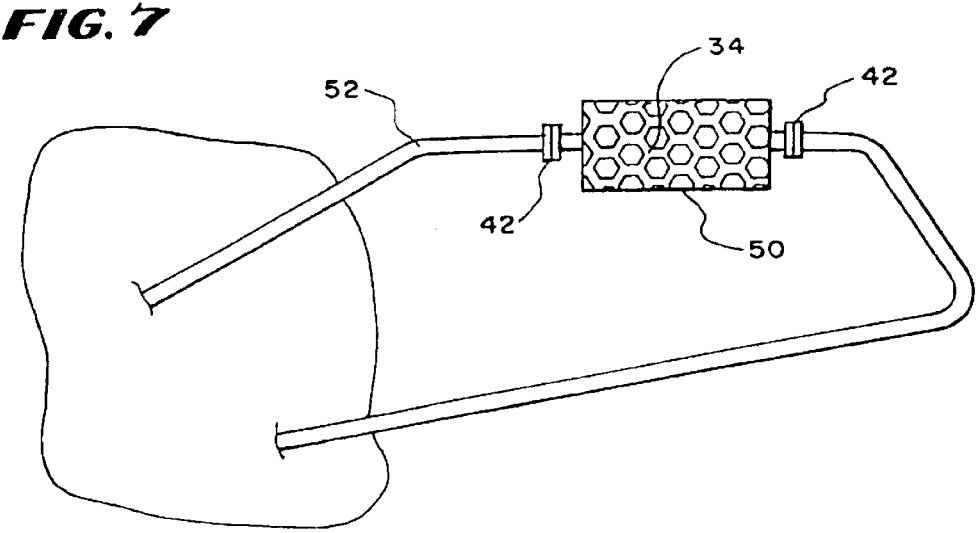
FIG. 7 is a side view of an indwelling catheter having an in-line device that contains an adsorption medium for removing cytokines or other species of pro-inflammatory or anti-inflammatory stimulators or mediators from the blood, making possible an ambulatory treatment regime.

As FIG. 7 shows, either device 18 or 30 can comprise a component 50 that is intended to be coupled to an indwelling catheter 52, that is surgically fitted to the individual undergoing treatment. The catheter 52 is surgically attached to the circulatory system of the individual, e.g., between an artery and a vein, to form a loop through which the blood continuously circulates. In this arrangement, the component 50 carries the adsorption medium 34 that serves to remove cytokines or other species of pro-inflammatory or anti-inflammatory stimulators or mediators from the individual's blood traversing the catheter 52. As a part of an indwelling blood circulation loop, the component 50 removes cytokines or other species of pro-inflammatory or anti-inflammatory stimulators or mediators continuously on a daily basis, as the individual ambulates and carries on life's activities outside of a treatment facility.

The component 50 can be configured to be an external or internal exchangeable device that can be releasable coupled to the indwelling catheter 52, e.g., by use of luer fittings 42, in the manner generally shown in FIGS. 4A and 4B. Alternatively, the wall of the indwelling catheter 52 can itself be impregnated with the adsorption medium 34, as generally shown in FIG. 5.

The component 50, in association with an indwelling catheter 52, makes possible a continuous, ambulatory treatment to remove cytokines or other species of pro-inflammatory or anti-inflammatory stimulators or mediators. This treatment modality would have particular application for those "at risk" individuals whose disease states are caused by or otherwise correlate with chronic, increased physiologic cytokine activity or other unregulated inflammatory response condition. The component 50 provides a new form of ambulatory treatment for, e.g., rheumatoid arthritis; or lung disease such as emphysema or asthma; or adult respiratory distress syndrome (ARDS); or autoimmune disease; or AIDS. The component 50 serves to maintain a reduced population of cytokines or other species of pro-inflammatory or anti-inflammatory stimulators or mediators, by continuously removing cytokines or other species of pro-inflammatory or anti-inflammatory stimulators or mediators from the blood circulation. The component 50 can be used alone or in combination with other treatment modalities for the disease condition.

C. Integrated Composite Devices

Figure 8:
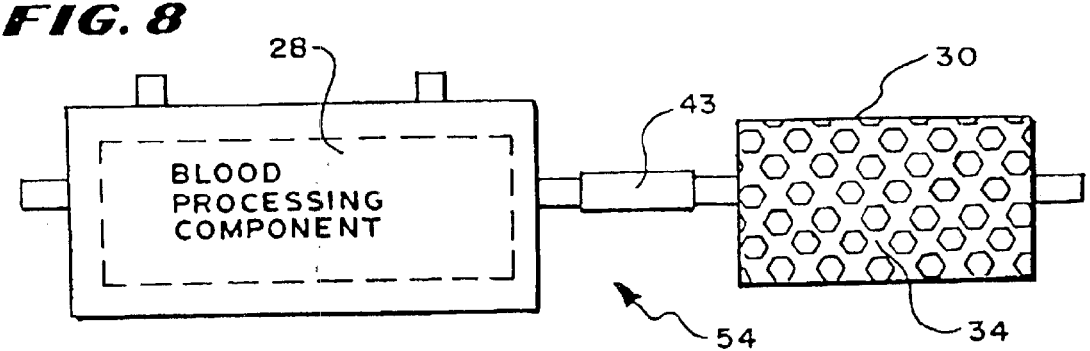
FIG. 8 is a side section view of a composite treatment module which integrates a device for removing cytokines or other species of pro-inflammatory or anti-inflammatory stimulators or mediators from the blood with a blood processor, the removal device being shown connected by intermediate tubing downstream from the blood processor.
Figure 9:
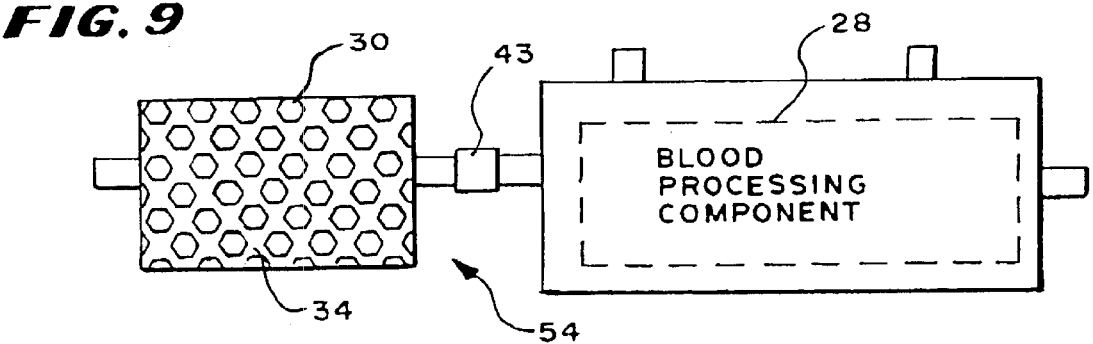
FIG. 9 is a side section view of a composite treatment module which integrates a device for removing cytokines or other species of pro-inflammatory or anti-inflammatory stimulators or mediators from the blood with a blood processor, the removal device being shown connected by intermediate tubing upstream from the blood processor.

FIGS. 8 and 9 show an absorption device 30 of a type shown in FIG. 3, integrally coupled by intermediate tubing 43 to a blood processor 28. Together, the device 30, processor 28, and linking tubing 43 form a composite blood treatment module 54 that is supplied to a user as an integrated unit.

The composite module 54 can be arranged so that the absorption device 30 is integrally coupled in a downstream flow direction to the blood processor 28 (as FIG. 8 shows), or, alternatively arranged, in an upstream flow direction to the blood processor 28 (as FIG. 9 shows). In yet another arrangement, the adsorption device 30 can be placed both upstream and downstream of the blood processor 28.

The module 54 can perform different blood processing functions in association with a blood adsorption function, e.g., to remove cytokines or other species of pro-inflammatory or anti-inflammatory stimulators or mediators, depending upon the operational capabilities of the blood processor 28. The processor 28 can be configured to perform diverse functions, e.g., hemodialysis, or hemofiltration, or membrane separation of plasma from whole blood, or blood filtering (e.g., to remove leukocytes), or ionic exchange, etc., or combinations thereof.

Figure 10A:
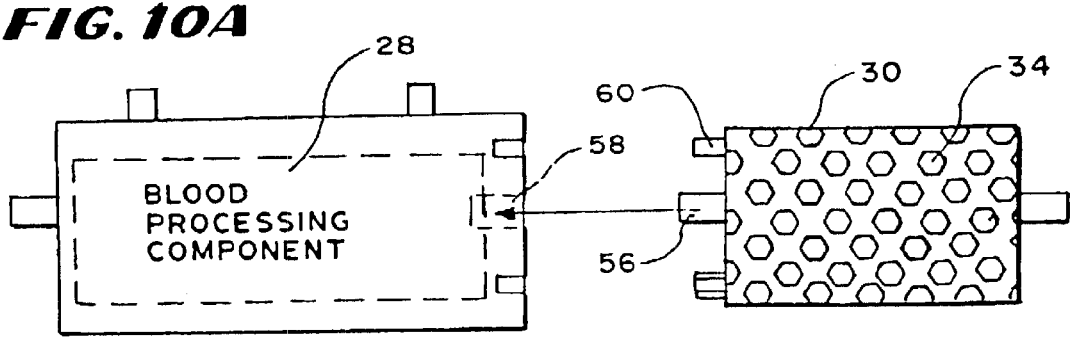
FIG. 10A is a side section view of a composite treatment module which integrates a device for removing cytokines or other species of pro-inflammatory or anti-inflammatory stimulators or mediators from the blood with a blood processor, the removal device and the blood processor comprising separate units adapted to be joined together for use.
Figure 10B:
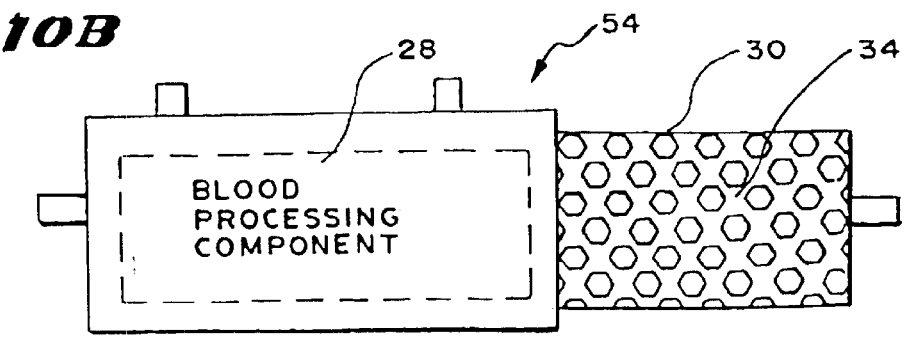
FIG. 10B is the composite treatment module shown in FIG. 10B after being joined together for use.

As FIGS. 10A and 10B show, the adsorption device 30 can be more intimately attached to the blood processor 28 to form the module 54 without use of intermediate tubing 43. In this arrangement (see FIG. 10A), both the adsorption device 30 and processor 28 are manufactured as separate units. The adsorption device 30 and processor 28 are configured with, e.g., a tubular male fitting 56 on the device 30 that mates with a female fitting 58 in the processor 28. The fittings 56 and 58 couple the device 30 and the processor 28 together in fluid flow communication, as FIG. 10B shows.

Of course, the mating configuration of the fittings 56 and 58 can be reversed, so that the device 30 includes a female fitting 58 and the processor 28 includes the male fitting 56. Furthermore, other attachment configurations, e.g., screw fit, keyed fittings, etc., can be used. Mating stabilization struts 60 may also be provided to further lock the device 30 and processor 28 together.

By manufacturing the adsorption device 30 and separator 28 separately, and then joining them together to form an integrated module 54, different sterilization processes may be used. For example, the device 30 and adsorption medium 34 may be sterilized by a first sterilization process, e.g., hot water or steam or external irradiation, whereas the processor 28 may be sterilized by a second, different sterilization process, e.g., EtO sterilization. This modular arrangement thereby accommodates the choice of biomaterials for the adsorption medium 34 and the functional component of the processor 28 having different physical properties best suited for their particular functional objections, and not constrained by similar sterilization requirements. The arrangement shown in FIGS. 8 and 9 also accommodates different sterilization techniques prior to joining the device 30 and processor 28 with the tubing 43.

As with the embodiments shown in FIGS. 8 and 9, the fittings 56 and 58 can configured to join the device 30 in an upstream flow direction to the blood processor 28, or (as FIG. 10B shows) in a downstream flow direction to the blood processor 28, or at both upstream and downstream ends of the blood processor 28.

The device 30 may be integrally coupled to the processor 28 during manufacturing, and be supplied to the customer as an integrated module 54 (as FIG. 10B shows). Alternatively, the device 30 and processor 28 may be supplied separately to the customer (in the manner shown in FIG. 10A), who is instructed to join the adsorption device 30 to the processor 28 by plugging the fittings 56 and 58 together at time of use.

Figure 11:
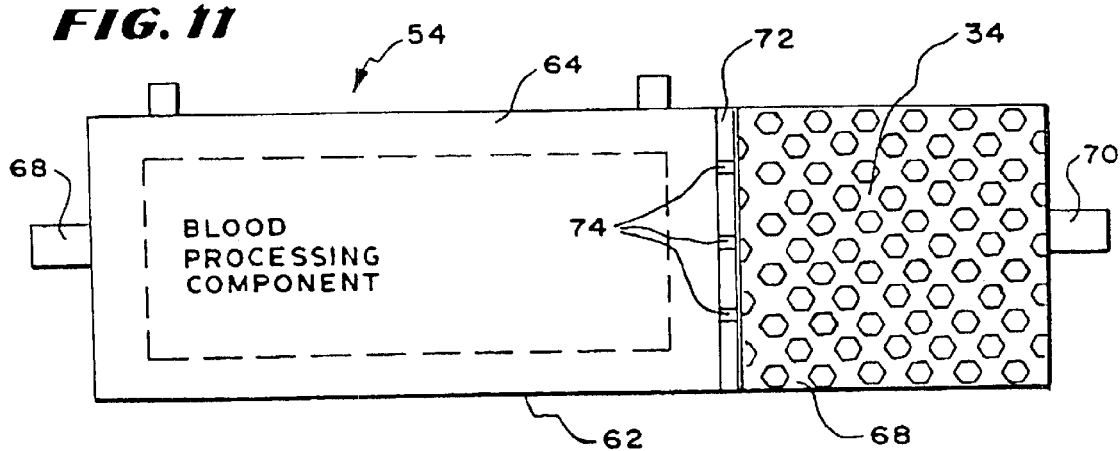
FIG. 11 is a side section view of a composite treatment module which integrates a device for removing cytokines or other species of pro-inflammatory or anti-inflammatory stimulators or mediators from the blood with a blood processor, the module comprising a common housing compartmentalized into two chambers, one chamber containing the blood processing component and the other chamber containing an adsorption medium for removing cytokines or other species of pro-inflammatory or anti-inflammatory stimulators or mediators from the blood being processed.

As FIG. 11 shows, the adsorption device 30 can be even more intimately associated with the blood processor by placing the processor 28 and device 30 within the confines of a single housing 62. The single housing 62 has an inlet port 68 and an outlet port 70. In this arrangement, an interior partition wall 72 in the housing 62 compartmentalizes the housing 62 into a first compartment 64 (which communicates with the inlet port 68) and a second compartment 66 (which communicates with the outlet port 70). One or more openings 74 in the interior wall 72 open flow communication between the first and second compartments 64 and 66.

Each compartment 64 and 66 can contain either the functional component of the processor 28 or the adsorption medium 34. In the embodiment shown in FIG. 11, the functional component of the processor 28 is contained in the first compartment 64, and the adsorption medium 34 is contained in the second compartment 66. Of course, the arrangement of the materials contained in the compartments 64 and 66 can be reversed. The housing can also be partitioned to place the adsorption medium 34 at both the inlet and outlet sides of the blood processor 28, sandwiching the functional component of the blood processor 28 between it.

This arrangement requires the selection of materials for the processor 28 and adsorption medium 34 that accommodate the same sterilization process, e.g., hot water sterilization.

It should be appreciated that the various composite structures 54 just discussed, which join an adsorption device 30 with a blood processor 28, are not limited to a particular adsorption function for the adsorption device 30. That is, while the adsorption device 30 has be earlier described in this application the context of the removal of cytokines or other species of pro-inflammatory or anti-inflammatory stimulators or mediators, the adsorption device 30 can, in association with the processor 28, carry out other functions as well. For example, when the processor 28 takes the form of a hemodialyzer, the adsorption device 30 can serve the function of selectively adsorbing middle molecular weight proteins (e.g., beta-2 macroglobulin) that conventional hemodialysis membrane do not efficiently remove.

D. Adsorption Medium

The adsorption medium 34 can be variously constructed. In the illustrated embodiment (see, e.g., FIG. 3), the adsorption medium 34 desirable includes a group of porous polymeric particles 76, which are formed to selectively retain cytokines or other species of pro-inflammatory or anti-inflammatory stimulators or mediators. Taking into account the physical proportions of cytokines or other species of pro-inflammatory or anti-inflammatory stimulators or mediators, the polymeric particles 76 of the medium 34 are predominantly mesoporous, with a pore size ranging from 2 to 70 nm, and preferably from 5 to 50 nm.

Figure 12:
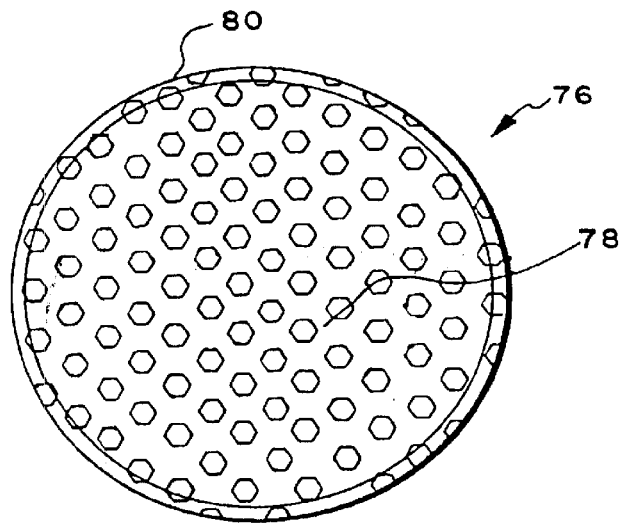
FIG. 12 is a side section view of an adsorption particle that can be used in association with the systems shown in FIGS. 1 and 2 for selectively adsorbing cytokines or other species of pro-inflammatory or anti-inflammatory stimulators or mediators from the blood.

As FIG. 12 best shows, each polymer particle 76 desirably possesses a porous hydrophobic core 78. The pores are sized to provide close contact between the cytokines or other species of pro-inflammatory or anti-inflammatory stimulators or mediators and the hydrophobic surface of the pores.

The surface of the hydrophobic particles 76 can be modified to provide a hydrophilic coating 80, which imparts a high degree of biocompatibility with the human organism, and, in particular, the blood. This biocompatibility can be expressed in terms of a biocompatible index, as will be decribed in greater detail later. The hydrophilic coating 80 is desirably thin and permeable so as to allow penetration of cytokines or other species of pro-inflammatory or anti-inflammatory stimulators or mediators to the hydrophobic porous core 78 of the particles 76.

The hydrophobic cores 78 of the particles 76 can be composed, for example, of crosslinked polymeric materials prepared by polymerization or copolymerization of the following monomers: styrene, ethylstyrene, α-methylstyrene, divinylbenzene, di isopropenyl benzene, trivinylbenzene, alkyl methacrylate as methyl methacrylate, butyl methacrylate. The hydrophilic biocompatible coating 80 of the particles 76 can be composed for example of the following materials: polyvinylpyrrolidone, polyhydroxyethyl methacrylate, carboxymethylcellulose, polyurethane.

In a device of the type shown in FIG. 3, the particles 76 are sized, taking into account the size of the device, to obtain a desired flow rate through the device. As an example, given a device size of 400 ml, the particles 76 are sized greater than 300 μm in diameter to present an effective surface area to the blood of about 500 $m^2$/gram of adsorption medium 34 used.

Particles 76 having the characteristics described also selectively adsorb superantigens. Superantigens are low molecular weight proteins that are toxic. Superantigens are produced by organisms and are strong activators of the immune system and cytokine production. The presence of superantigens can therefore also contribute to increased levels of cytokines or other species of pro-inflammatory or anti-inflammatory stimulators or mediators. The concurrent removal by the particles of both cytokines or other species of pro-inflammatory or anti-inflammatory stimulators or mediators and superantigens enhances the overall therapeutic function of the adsorption medium 34.

REPRESENTATIVE ADSORPTION MEDIUM

EXAMPLE 1

In one representative embodiment, the adsorption medium 34 can include particles or beads formed from hypercrosslinked polystyrene-type resins. The surface of the beads is desirably modified to prevent absorption of large proteins and platelet and to minimize activation of blood complement system, without affecting noticeably accessibility of an inner absorption space of the beads for small and middle-sized molecules. The particles or beads can comprise, e.g., styrene-divinylbenzene copolymers subjected to an extensive crosslinking in a swollen state with bifunctional crosslinking agents, such as monochlorodimethyl ether or p-xylylene dichloride. Alternatively, the particles or beads can comprise styrene-divinylbenzene copolymers subjected to chloromethylation and post-crosslinking. Alternatively, the material can comprise a porous hydrophobic acrylic polymer or a mesoporous ethylstyrene-divinylbenzene copolymer.

The surface modification can be accomplished is various ways, e.g., (i) by depositing on the surface of the particles or beads high molecular weight poly (N-trifluoroalkoxy) phosphazene, by treating the beads with a solution of phosphazene in an organic solvent and evaporating the solvent; or (ii) electrostatically binding of heparin from its aqueous solution onto the beads whose chloromethyl groups have been substituted by amino functions through a reaction with an amine, such as 2-ethanol amine; (iii) substituting chloromethyl groups on the surface of the beads with 2-ethanol amine ligands and covalently binding heparin to the ligands via a material such as a glutare dialdehyde and hexamethylene diisocyanate moiety, and coupling groups consisting of excessive pendant aldehyde groups and isocyanate groups with L-aspartic acid; or (iv) substituting chloromethyl groups with a material such as 2-ethanol amine and ethylene glycol ligands, activating the ligands with a material such as glutare dialdehyde and hexamethylene diisocyanate, and covalently binding hydrophilic polyethylene glycol chains; or (v) covalently binding hydrophilic polyethylene glycol chains through reacting of sodium alcoholates of the latter with polystyrene chloromethyl groups; or (vi) covalently binding hydrophilic chains of chitosan through reacting of amino groups of the latter with polystyrene chloromethyl groups; or (vii) substituting chloromethyl groups with ligands such as 2-ethanol amine ligands or ethylene glycol ligands, activating the ligands with phosphorus oxychloride, and covalently binding hydrophilic moieties such as choline, serine and 2-ethanol amine.

Further details regarding the composition of particles or beads of this type can be found in U.S. Pat. No. 5,904,663, which is incorporated herein by reference.

REPRESENTATIVE ADSORPTION MEDIUM

EXAMPLE 2

In another representative embodiment, the adsorption medium 34 can include particles or beads formed from a porous hydrophobic divinylbenzene copolymer with comonomers selected from the group of styrene, ethylstyrene, acrylonitrile, and buthyl methacrylate. Such particles or beads initially have surface exposed vinyl groups, which are chemically modified to impart improved biocompatibility, so as to form different surface exposed functional groups, such as polymers of 2-hydroxyethyl methacrylate, N-vinylpyrrolidine, N-vinylcaprolactame, or N-acrylamide. The surface exposed functional groups can be products of oxidation of the vinyl groups to expoxy groups and subsequent addition of polar compounds selected from the group of water, ethylene glycol, primary or secondary amines, and 2-hydroxethyl-amine. Alternatively, the surface exposed functional groups can be the products of oxidation of the vinyl groups to epoxy groups, the subsequent addition of primary or secondary amines or 2-hydroxyethylamine, and the deposit of high-molecular-weight poly (trifluoroethoxy) phosphazene.

Further details regarding the composition of particles or beads of this type can be found in U.S. Pat. No. 6,114,466, which is incorporated herein by reference.

REPRESENTATIVE ADSORPTION MEDIUM

EXAMPLE 3

In another representative embodiment, the adsorption medium 34 can include particles or beads formed by polymerization of aromatic divinyl compounds, such as p- or m-divinylbenzene or mixtures thereof, or their copolymerization with aromatic monovinyl compounds, such as styrene, methylstyrene, ethylvinylbenzene and vinylbenzylchloride, in the presence of porogens or mixtures of porogens with properties close to those of θ-solvents. The porogens can comprise, e.g., cyclohexane, cyclohexanone and other θ-solvents for polystyrene. Alternatively, the porogens can comprise θ-solvents composed of mixtures of a good solvent for polystyrene, such as toluene, benzene, ethylene dichloride, propylene dichloride, tetrachloroethene, dioxane and methylene dichloride, and a non-solvent for polystyrene, such as aliphatic hydrocarbons, aliphatic alcohols and aliphatic acids.

Such hypercrosslinked polymeric adsorbents exhibit a combination of micropores, mesopores and macropores. The adsorbents may further be functionalized to enhance their biocompatibility.

Further details regarding the composition of particles or beads of this type can be found in U.S. patent application Ser. No. 09/143,407, filed Aug. 28, 1998, entitled "Hypercrosslinked Polymeric Material for Purification of Physiological Liquids of Organism, a Method for Producing the Material," which is incorporated herein by reference.

1. Biocompatibility Index

Desirably, the adsorption medium 34 is characterized by a biocompatibility index that indicates a physiologically negligible production of cytokines or other species of pro-inflammatory or anti-inflammatory stimulators or mediators in the blood as a result to exposure to the medium. Thus, the adsorption medium 34, which beneficial serves to remove cytokines or other species of pro-inflammatory or anti-inflammatory stimulators or mediators from the blood, does not itself produce an offsetting result of generating additional cytokines or other species of pro-inflammatory or anti-inflammatory stimulators or mediators.

The biocompatibility index can be expressed as a dimensionless, numeric quantity, which reflects the degree to which a prescribed battery of blood characteristics change as a result of contact between the blood and the adsorption medium.

The prescribed battery of blood characteristics that the biocompatibility index encompasses rely upon several selected blood indicators, which quantify, based upon contact between the blood and a given adsorption medium, (i) the degree to which the numbers of cellular blood components (red blood cells, white blood cells, and platelets) are diminished; (ii) the degree to which leukocytes are activated; (iii) the degree to which complement activation occurs; (iv) the degree to which hemolysis occurs; and (v) the degree to which clot formation is induced.

Indicator (i) is ascertained by Coulter Counter for red blood cells, white blood cells, and platelets (this indicator this comprises three individual indicators).

Indicator (ii) is ascertained by measuring polymorphonuclear leukocyte elastase (PMN Elastase) concentrations using standard laboratory techniques (e.g., PMN Elastase, Merck Immunoassay, Merk KgaA, Darmstadt, Germany).

Indicator (iii) is ascertained by measuring anaphylatoxin C3a-desArg concentrations using standard laboratory techniques (e.g., Elisa, Progen Biotechnik GmbH, Heidelberg, Germany).

Indicator (iv) is ascertained by determining the concentrations of Lactate dehydrogenase (LDH) by standard methods of clinical chemistry.

Indicator (v) is ascertained by measuring the concentrations of thrombin-antithrombin-complex (TAT) using standard laboratory techniques (e.g.,Enzygnost-TAT micro Elisa, Dade Behring Marburg GmbH, Marburg, Germany).

There are therefore a total of seven indicators within the battery of indicators for the Biocompatibility Index: (1) White Blood Cell Count; (2) Red Blood Cell Count; (3) Platelet Count; (4) PMN Elastase Concentration; (5) LDH Concentration; (6) C3a-desArg Concentration; and (7) TAT Concentartion. These indicators are listed in Table 1, below.

In deriving the biocompatibility index, the technician selects a housing for the media that is made of an acceptable biocompatible material that possesses a biocompatibility comparable to conventional medical grade plastics (e.g., polyvinylchloride, polyurethane, polyester, etc) or glass. The technician characterizes the blood according to the battery of indicators after passing the blood through the housing in an empty condition, i.e., a housing that contains no absorption medium.

The technician uses heparin to anticoagulate the blood in a final concentration of 1.0 IU heparin/ml blood. Other types of anticoagulant, such as nafamosat, may be used. However, citrate anticoagulant is not be to used, alone or in combination with the prescribed amount of heparin in deriving the biocompatibility index, because the presence of citrate will mask changes in thrombogenicity and complement activation that may arise due to contact with the medium, thereby leading to false results.

Figure 23:
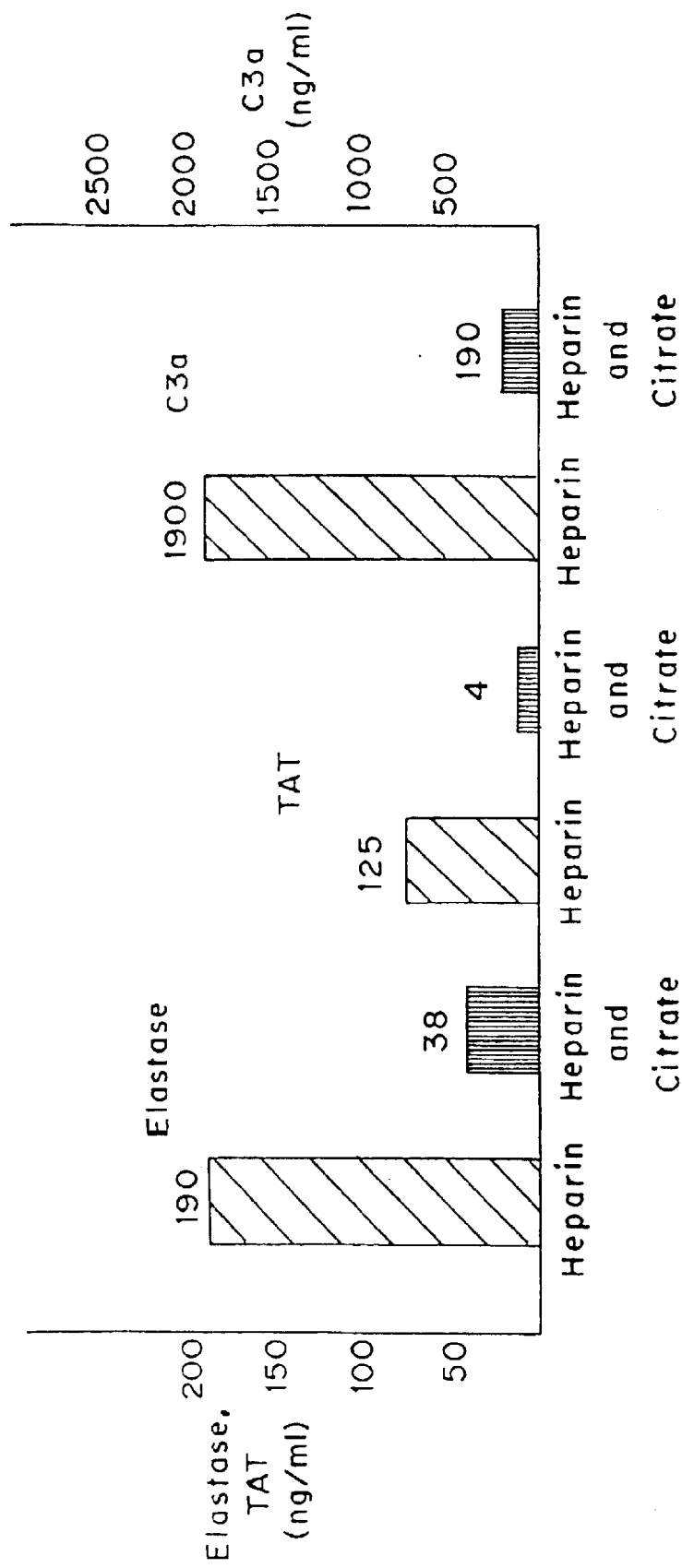
FIG. 23 is a chart summarizes the results of hemocompatibility testing conducted by Bosch et al of a polyacrylate gel adsorbant material (for the selective adsorption of low-density lipoproteins), based upon contact with blood that was anticoagulated either only with heparin or with a mixture of heparin and citrate.

FIG. 23 summarizes the results of hemocompatibility testing conducted by Bosch et al of a polyacrylate gel adsorbant material (for the selective adsorption of low-density lipoproteins), based upon contact with blood that was anticoagulated either only with heparin or with a mixture of heparin and citrate (Bosch et al, *Artif Organ* 17(7) 640-52 1993). FIG. 23 demonstrates that, with respect to the thrombogenicity and complement activation indicators —PMN Elastase (indicating the degree to which leukocytes are activated); thrombin-antithrombin-complex TAT (indicating the degree to which clot formation is induced); and anaphylatoxin C3a-desArg (indicating the degree to which complement activation occurs)—each indicator level reads high (denoting thrombogenicity and complement activation) when only heparin anticoagulant is used. The mixture of citrate with heparin masks the actual indicator levels in a significant way. FIG. 23 shows that, by binding calcium (an important co-factor in many hemocompatibility reactions), the presence of citrate lowers the indicator levels, so that they no longer reflect the actual changes in thrombogenicity and complement activation that arise due to contact with a given medium.

The forgoing protocol provides the background or baseline sample, against which the magnitude of changes due to the presence of a given adsorption medium within the housing can be ascertained and scored.

In deriving the biocompatibility index, the technician also characterizes the blood according to the battery of indicators after passage through the selected housing that contains the absorption medium. As before, the technician uses heparin to anticoagulate the blood in a final concentration of 1.0 IU heparin/ml blood. For the reasons stated above, citrate anticoagulant is not be to used in deriving the biocompatibility index, alone or in combination with the prescribed amount of heparin.

Figure 16:
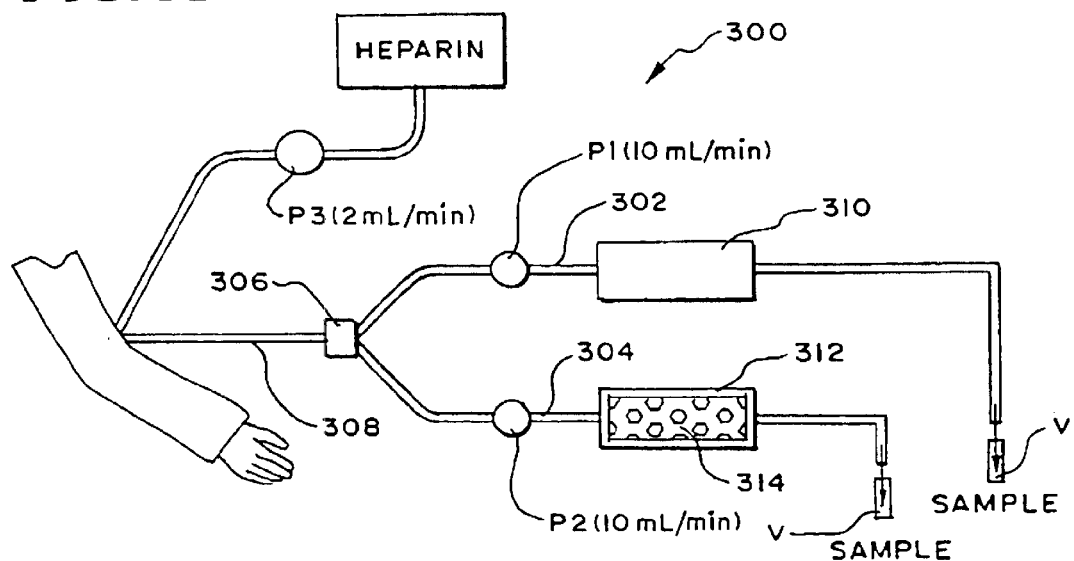
FIG. 16 is a schematic diagram of a test system that is used to characterize the biocompatibility index of a given adsorbant medium.

In carrying out the steps just described, the technician assembles a test system 300 as shown in FIG. 16. The test system 300 comprises two parallel channels 302 and 304 connected by a y-connector 306 to a blood line 308. A housing 310 and 312 is coupled in each channel, respectively 302 and 304. The housing 310 is empty (i.e., free of adsorption medium), and the housing 312 contains the adsorption medium 314. The blood line 308 can be coupled, e.g., to the antecubital vein of a healthy volunteer. The access system desirably allows for continuous heparinization at the tip of the inserted cannula or needle to avoid systemic heparinzation. Peristaltic pumps P1 and P2 in the channels 302 and 304 (or a single, double tube peristaltic pump) convey the blood through the housings 310 and 314. An infusion pump P3 meters heperin, to achieve a final heparin concentration of 1.0 IU/ml.

The pumps P1, P2, and P3 are started simultaneously. On-line blood perfusion of the two channels 302 and 304 is maintained through each housing 310 and 312. The speeds of the pumps P1 and P2 are adjusted to 10 mL/min through each housing 310 and 312. Blood samples are collected at the outlet of each channel 302 and 304 after 5, 10, 15, and 25 minutes of perfusion directly into specially prepared polypropylene vials V stored on ice. The blood samples are analyzed for the selected indicators immediately. Blood counts are corrected for hemodilution due to the addition of heparin.

The cell count indicators are corrected by the following formula: $X_{corr} = X$ times $(hct_{pre}/hct_t$, where $X_{corr}$ is the corrected parameter, X is the measured value of the parameter at time point t, $hct_{pre}$ is the hematocit pre value (t=0), and $hct_t$ is the hematocrit at time point t.

The plasma indicators for PMN Elastase Concentration, LDH Concentration, C3a-desArg Concentration, and TAT Concentartion are corrected by the following formula: $X_{corr} = X$ times $(1-hct_t/1-hct_{pre}$, where $X_{corr}$ is the corrected plasma parameter, X is the measured value of the plasma parameter at time point t, $hct_{pre}$ is the hematocit pre value (t=0), and $hct_t$ is the hematocrit at time point t.

The technician reviews the assembled indicators to ascertain, for each indicator, the maximum difference between the indicator values over 25 ml of blood flow of the blood passed through the housing 310 (without the medium—baseline) and the blood passed through the housing 312 containing the medium 314. For each indicator, the technician expresses the maximum change as a percentage, relative to the baseline value.

The technician then scores the percentage change for each indicator as a dimensionless numeric quantity 1, 2, or 3, depending upon the magnitude of the percentage change, in accordance with Table 1. In Table 1, a percentage change equal to or less than a prescribed minimum for a given indicator is scored as a 1, signifying a most desirable degree of biocompatibility. In Table 1, a percentage change greater than a prescribed maximum for a given indicator is scored as a 3, signifying a least desirable degree of biocompatibility. In Table 1, a percentage change between the prescribed minimum and the prescribed maximum for a given indicator is scored as a 2, signifying an acceptable degree of biocompatibility, albeit not the most desired.

TABLE 1

The Biocompatibility Index Score Table

| Blood Indicator | Numeric Scores | | |
|---|---|---|---|
| | 1 (Signifying Most Desired Degree of Biocompatibility) | 2 (Signifying an Acceptable Degree of Biocompatibility) | 3 (Signifying a Least Desired Degree of Biocompatibility) |
| Loss of White Blood Cells | Maximum Difference Between Baseline and Medium (25 ml) ≤15% | Maximum Difference Between Baseline and Medium (25 ml) >15% ≤20% | Maximum Difference Between Baseline and Medium (25 ml) >20% |
| Loss of Red Blood Cells | Maximum Difference Between Baseline and Medium (25 ml) ≤15% | Maximum Difference Between Baseline and Medium (25 ml) >15% ≤20% | Maximum Difference Between Baseline and Medium (25 ml) >20% |
| Loss of Platelets | Maximum Difference Between Baseline and Medium (25 ml) ≤15% | Maximum Difference Between Baseline and Medium (25 ml) >15% ≤20% | Maximum Difference Between Baseline and Medium (25 ml) >20% |
| PMN Elastase Concentration | Maximum Difference Between Baseline and Medium (25 ml) ≤15% | Maximum Difference Between Baseline and Medium (25 ml) >15% ≤20% | Maximum Difference Between Baseline and Medium (25 ml) >20% |
| LDH Concentration | Maximum Difference Between Baseline and Medium (25 ml) ≤15% | Maximum Difference Between Baseline and Medium (25 ml) >15% ≤20% | Maximum Difference Between Baseline and Medium (25 ml) >20% |
| C3a-desArg Concentration | Maximum Difference Between Baseline and Medium (25 ml) ≤20% | Maximum Difference Between Baseline and Medium (25 ml) >20% ≤25% | Maximum Difference Between Baseline and Medium (25 ml) >25% |
| TAT Concentration | Maximum Difference Between Baseline and Medium (25 ml) ≤15% | Maximum Difference Between Baseline and Medium (25 ml) >15% ≤20% | Maximum Difference Between Baseline and Medium (25 ml) >20% |

After scoring each indicator with a numeric quantity of 1, 2, or 3, the technician adds the numeric quantities scored for all the indicators to obtain a total. The total constitutes the biocompatibility index for the given adsorption medium.

The Biocompatibility Index for a given material is a reliable indicator of blood compatibility. There is a strong correlation between the value of the Biocompatibility Index, derived in the manner just described, and the ability of given material to selectively remove targeted proteins from the blood without significant destruction of cellular components and hemolysis and without significant clot formation (i.e., low thrombogenicity). Materials characterized by a Biocompatibility Index equal to or less than 14, and, most desirably, by a Biocompatible Index not greater than 7, contact the blood with no significant loss of blood cells, no significant hemolysis, no significant activation of luekocytes or monocytes, and, at most, only very mild complement activation, even with the use of heparin as the sole anticoagulant. Because such materials are not likely to induce the generation of cytokines or other species of pro-inflammatory or anti-inflammatory stimulators or mediators, they are well suited for use to remove cytokines or other species of pro-inflammatory or anti-inflammatory stimulators or mediators from the blood, blood products, or physiologic fluids.

On the other hand, materials characterized by a Biocompatibility Index greater than 14, contact the blood with adverse effects in terms of significant blood cell loss, or significant hemolysis, or significant leukocyte activation, or significant compliment activation, or significant combinations thereof. Such materials are therefore likely to induce the generation of cytokines or other species of pro-inflammatory or anti-inflammatory stimulators or mediators and are not acceptable for use to remove cytokines or other species of pro-inflammatory or anti-inflammatory stimulators or mediators

E. Multiple Functionality

As previously discussed, the devices, systems, and methods are directed to the removal of cytokines or other species of pro-inflammatory or anti-inflammatory stimulators or mediators to reduce levels of such agents in the blood in situations where abnormal levels of such agents occur, or during events that do induce or have the potential for inducing abnormal production of cytokines or other species of pro-inflammatory or anti-inflammatory stimulators or mediators. In this way, the devices, systems, and methods serve to control, reduce, or alleviate the severity of many physiologic conditions and disease states that are associated with abnormal levels of cytokines or other species of pro-inflammatory or anti-inflammatory stimulators or mediators.

It should be appreciated that the devices, systems, and methods can be adapted to perform other functions in tandem with removal of cytokines or other species of pro-inflammatory or anti-inflammatory stimulators or mediators as well.

Figure 13:
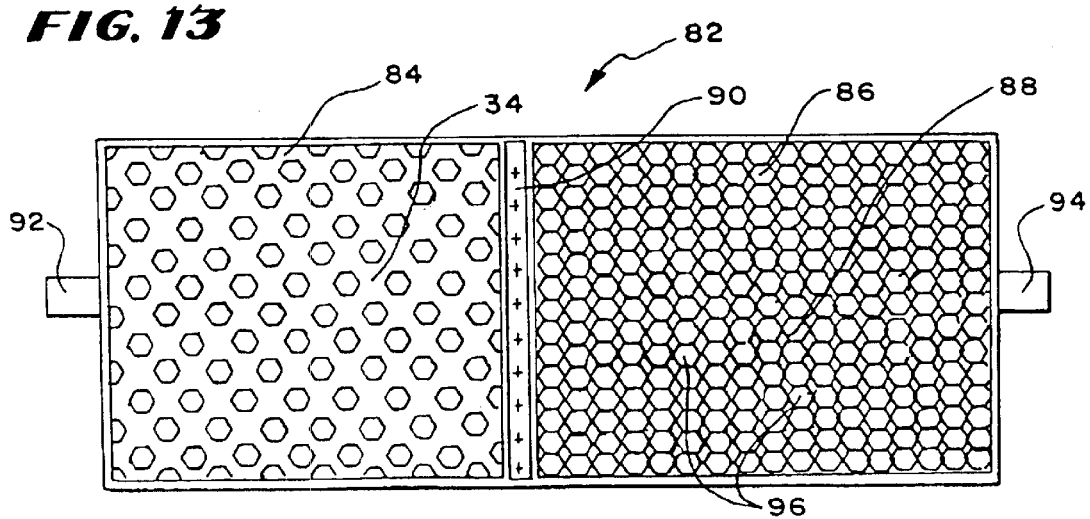
FIG. 13 is a side section view of a device that is usable in association with the systems shown in FIGS. 1 and 2 for removing both cytokines or other species of pro-inflammatory or anti-inflammatory stimulators or mediators and other targeted proteins or toxins from the blood.

FIG. 13 shows a device 82 that is usable in association with the systems and methods previously discussed to provide adsorption of both cytokines or other species of pro-inflammatory or anti-inflammatory stimulators or mediators and other material or materials from the blood. The device 82 includes a first compartment 84, which contains the adsorption medium 34, previously described, to remove cytokines or other species of pro-inflammatory or anti-inflammatory stimulators or mediators. The device 82 includes a second compartment 86, which contains a different medium 88, which can comprise an adsorption medium or an ion exchange medium, to remove another type of material from the blood. A partition 90 in the device 82 (e.g., made of a mesh material to accommodate fluid flow) separates the first compartment 84 from the second compartment 86. In use, the blood is conveyed into the device 82 through an inlet 92. The blood passes in succession through the adsorption medium 34 and the different, second medium 88. The blood exits the device 82 through an outlet 94. During passage, cytokines or other species of pro-inflammatory or anti-inflammatory stimulators or mediators are removed from the blood by the adsorption medium 34 and the other material is removed from the blood by the different, second medium 88. The order of passage through the mediums 34 and 88 can be reversed.

The adsorption medium 88 can be variously constructed depending upon the material intended to be removed.

1. Removal of LPS EndoToxin

For example, the adsorption medium 88 can be constructed to remove LPS endotoxin, which is released into the blood of an individual suffering from a gram-negative bacterial infection. In the blood, LPS endotoxin coalesce into vesicles ranging in size from 300,000 to 1,000,000 daltons. Phosphoryl groups contained within the LPS endotoxin give it an overall negative charge at physiologic pH. The release of LPS endotoxin into the blood can cause fever, low blood pressure, and organ failure.

As previously discussed, the presence of LPS endotoxin also stimulates the secretion of cytokines or other species of pro-inflammatory or anti-inflammatory stimulators or mediators. The presence of LPS endotoxin can therefore also contribute to increased levels of cytokines or other species of pro-inflammatory or anti-inflammatory stimulators or mediators, and even to the onset of a septic shock episode.

In the illustrated embodiment (see FIG. 13), the adsorption medium 88 includes a group of polymer particles 96 comprising hydrophobic porous core to which LPS endotoxin binds. To provide a reliable interaction between the endotoxin and the polymer core, the polymer particles have pores of a corresponding large size. For example, the size of the pores can be within the range of 20 to 150 nm, and preferably between 30 and 100 nm. The polymeric particles 96 are thus predominantly macroporous.

The polymer for the core of the particles 96 can be selected from the same group of materials as the polymer for the core 78 of the particles 76 of the adsorption medium 34, as before described.

Like the particles 76 of the first adsorption medium 34, the particles 96 of the adsorption medium 88 desirable include a hydrophilic coating or shell to provide biocompatibility, which is also desirably characterized by a high biocompatibility index. The coating material for the particles 96 can be selected from the same group of materials as the coating 80 for the particles 76 of the first adsorption medium 34.

In addition, the polymer particles 96 can also possess positively charged functional groups on the surface of the hydrophobic pores to further attract endotoxin through an ionic interaction. The amount of these positively charged groups desirably remains low, preferably below 1 meq/ml. Thus, the overall hydrophobic nature of the core of the polymeric particle is not compromised, so that hydrophobic interactions still remain the major mechanism of adsorption of LPS endotoxin. The positively charged functional groups covalently bonded to the surface of the pores of the polymeric particles 96 can be selected from the group composed of amino-, methylamino-, ethylamino-, dimethylamino-, diethylamino-, ethanolamino-, diethanolamino-, polyethylenimino-groups, imidazole, histamine, or basic amino acids as lysine, arginine, histidine.

2. Removal of Other Materials

The adsorption medium 88 can also be composed to selectively adsorb other targeted proteins or toxins that can be released into the blood as a result of injury or trauma, e.g., myoglobin, which can be released during a crush injury. The adsorption medium 88 can also be composed to selectively adsorb targeted chemical moieties that can be released into the blood as a result of injury or trauma, e.g., potassium, which can be released with myoglobin during a crush injury.

The device 18 or 30 can also be used in combination with other devices that remove materials from the blood other than by selective adsorption, e.g., by ion exchange effects.

Figure 14:
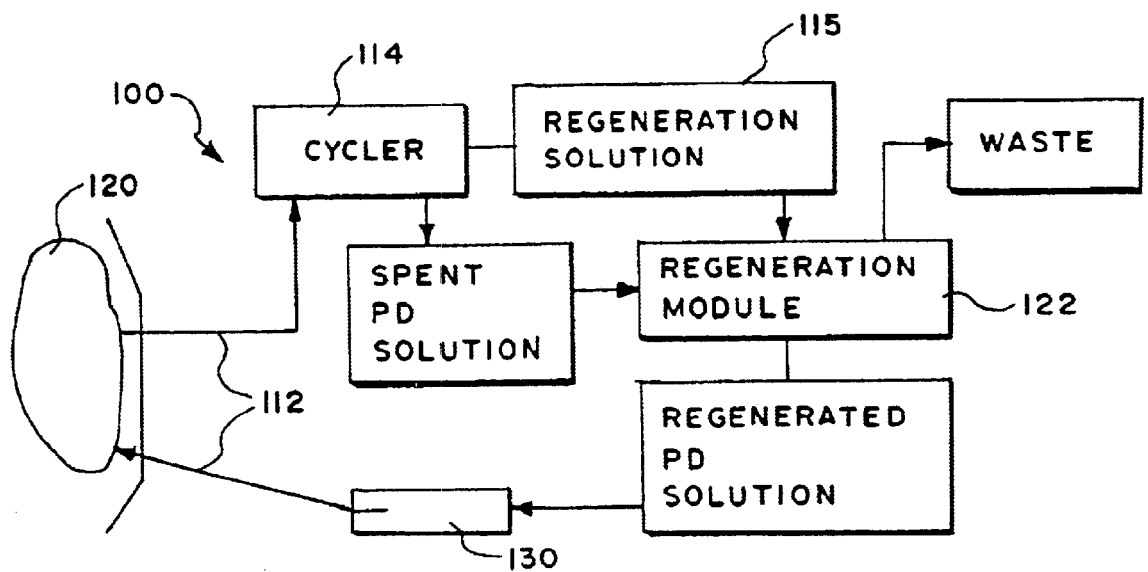
FIG. 14 is a schematic view of a system for removing cytokines or other species of pro-inflammatory or anti-inflammatory stimulators or mediators from a physiologic fluid, which takes the form of regenerated peritoneal dialysis solution.

III. Systems and Methods for Removing Cytokines or other Species of Pro-inflasmatory or Anti-inflammatory Stimulators or Mediators from Physiologic Fluids FIG. 14 shows an embodiment of a system 100 for removing cytokines or other species of pro-inflammatory or anti-inflammatory stimulators or mediators from a physiologic fluid. In this embodiment, the physiologic fluid comprises fresh peritoneal dialysis solution that has been regenerated from spent peritoneal dialysis solution.

As shown in FIG. 14, the system 100 is configured for conducting a form of automated peritoneal dialysis. The system 100 includes a cycler 114, to automatically infuse, dwell, and drain peritoneal dialysis solution to and from the patient's peritoneal cavity 120, typically at night while the patient is asleep.

The system 100 includes a peritoneal dialysis solution flow set 112 that establishes communication between the system 100 and the peritoneal cavity 120 of the patient. The cycler 114 interacts with the flow set 112, to pump peritoneal dialysis solution into and out of the patient's peritoneal cavity 120 in prescribed infuse, dwell, and drain cycles.

The flow set 112 includes an in-line regeration module 122. The cycler 114 circulates peritoneal dialysis solution, removed from the patient's peritoneal cavity 120, into the module 122 The cycler 114 also circulates a regeneration solution containing, e.g., electrolytes and/or buffering materials, from a source 115 into the module 122.

The module 122 includes a component, e.g., a membrane, that transports waste and uremic toxins from the spent peritoneal dialysis solution into the regeneration solution, while also transporting electrolytes and buffering materials from the regeneration solution 115 into the peritoneal dialysis solution. Typically, the regeneration fluid, laden with toxins and depleted of electrolytes and buffers, is sent to waste.

The module 122 thereby performs on-line regeneration of peritoneal dialysis solution. Upon regeneration, the cycler 114 re-circulates the peritoneal dialysis solution back to the peritoneal cavity 120 of the patient.

The spent peritoneal dialysis solution may carry cytokines or other species of pro-inflammatory or anti-inflammatory stimulators or mediators generated while the solution dwelled within the peritoneal cavity of the patient. Extracorporeal processing of the spent solution by the cycler 114 can also trigger additional production of cytokines or other species of pro-inflammatory or anti-inflammatory stimulators or mediators.

The system 100 therefore includes a device 130 that removes cytokines or other species of pro-inflammatory or anti-inflammatory stimulators or mediators from the physiologic peritoneal dialysis solution prior to its return to the patient's peritoneal cavity 120. The device 130 can be coupled to the system 100 either upstream or downstream of the regeneration module 122. In this arrangement, cytokines or other species of pro-inflammatory or anti-inflammatory stimulators or mediators are removed from the peritoneal dialysis solution either before or after regeneration, and prior to return to the regenerated solution to the peritoneal cavity 120 of the patient. This leads to overall reduced levels of cytokines or other species of pro-inflammatory or anti-inflammatory stimulators or mediators in the peritoneal dialysis patient.

It should be appreciated that the device 122 can be used in other peritoneal dialysis modalities where regeneration of peritoneal dialysis solution is performed.

Body fluids that are removed from and then recycled back to the body during a given treatment modality can also carry cytokines or other species of pro-inflammatory or anti-inflammatory stimulators or mediators, or cytokines or other species of pro-inflammatory or anti-inflammatory stimulators or mediators can be generated as a result of such treatment modalities. Treatment systems and methods exist for removing and recycling such fluids, e.g., lymphatic fluid, synovial fluid, spinal fluid, or cerebrospinal fluid. The devices, systems, and methods that embody this aspect of the invention, as just discussed in the context of peritoneal dialysis, can likewise be used in association with such treatment modalities, to remove cytokines or other species of pro-inflammatory or anti-inflammatory stimulators or mediators from the body fluids before, during, or after other forms of primary treatment.

Figure 15:
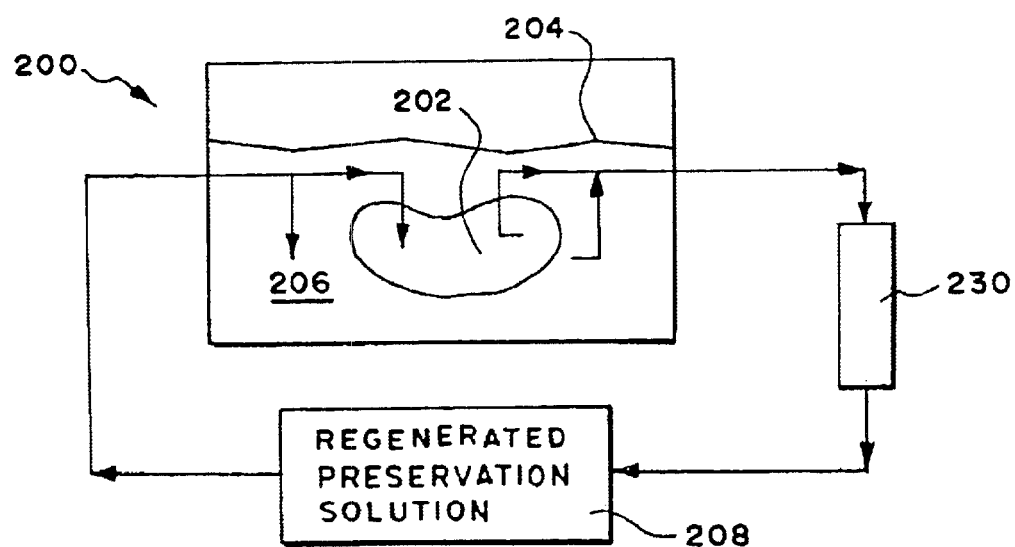
FIG. 15 is a schematic view of a system for removing cytokines or other species of pro-inflammatory or anti-inflammatory stimulators or mediators from a physiologic fluid, which takes the form of preservation solution for an organ awaiting transplantation.

FIG. 15 shows another embodiment of a system 200 for removing cytokines or other species of pro-inflammatory or anti-inflammatory stimulators or mediators from a physiologic fluid. In this embodiment, the physiologic fluid comprises preservation solution 206 for a harvested organ 202 awaiting transplantation.

As shown in FIG. 15, the system 200 includes a bath 204 holding the organ 202. The preservation solution 206 is circulated from a source 208 through the bath 204 and through the organ 202. FIG. 15 depicts a harvested kidney 202, but the organ can be any solid organ harvested for transplant.

The organ 202 may generate cyctokines or other species of pro-inflammatory or anti-inflammatory stimulators or mediators while immersed in the bath 204. The cytokines or other species of pro-inflammatory or anti-inflammatory stimulators or mediators will, in turn enter the preservation solution 206 contacting and perfusing the organ 202. Circulation of the preservation solution may also trigger additional production of cytokines or other species of pro-inflammatory or anti-inflammatory stimulators or mediators.

The system 200 therefore includes a device 230 that removes cytokines or other species of pro-inflammatory or anti-inflammatory stimulators or mediators from the preservation solution. The device 230 can be coupled to the system 200 either upstream or downstream of the bath 204. In this arrangement, cytokines or other species of pro-inflammatory or anti-inflammatory stimulators or mediators are removed from the preservation solution, so that the overall population of cytokines or other species of pro-inflammatory or anti-inflammatory stimulators or mediators to which the organ 202 is exposed prior to transplantation is minimized. This leads to overall reduced levels of cytokines or other species of pro-inflammatory or anti-inflammatory stimulators or mediators in the patient who receives the organ transplant.

Either device 120 or 230 can be constructed in generally the same fashion already described with respect to devices 18 or 30.

EXAMPLE 1

Blood Purification Using an Adsorption Medium to Restore Immunologic Stability

A study was conducted to demonstrate the ability of a biocompatible adsorption medium to selectively adsorb cytokines (TNF, IL-6, and IL-10) from the blood. The medium comprised particles (as generally shown in FIG. 12) formed of a core of hydrophobic, crosslinked porous divinylbenzene material coated with a thin, permeable biocompatible hydrophilic polyvinylpyrrolidone material. The core material of the particles possessed a mean pore size of about 16 nm. The particles were contained within a housing (as generally shown in FIG. 3)and presented a surface area to blood flow of about 650 sq.mg. The medium was obtained from RenalTech International, New York, N.Y. (BetaSorb™ Adsorption Medium).

The medium was tested in an experiment using in three animals subjected to cecal ligation and puncture (CLP) 18 hrs earlier. The animals tolerated treatment with the medium without difficulty. The cytokine response was characterized over the four hours of treatment (see FIG. 17).

Figure 17:
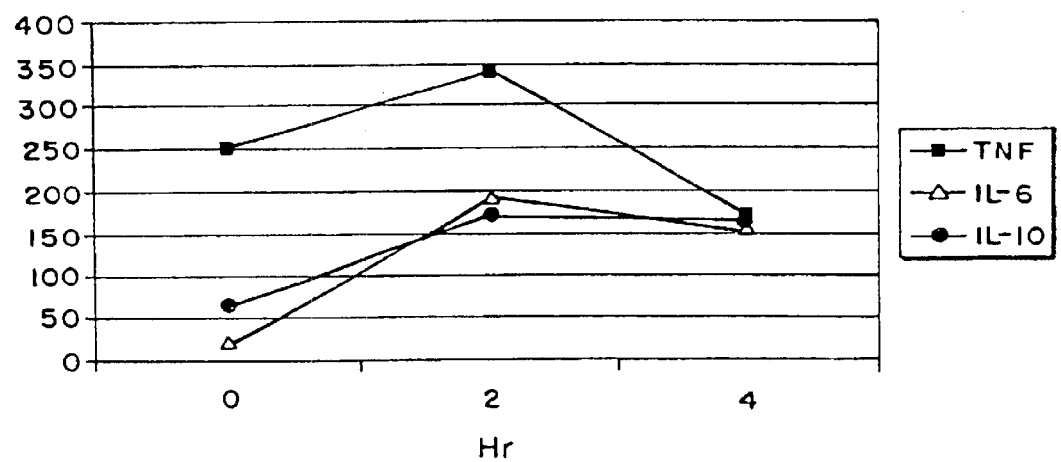
FIG. 17 is a graph plotting the cytokine response in the blood of a sepsis animal model as a result of treatment using a biocompatible adsorbant medium.

The results demonstrate that the medium removed all three cytokines from the blood. As FIG. 17 shows, there was a flattening out or even downward trend in the concentrations of TNF, IL-6 and IL-10 (in order to keep the scales similar, the units for TNF in FIG. 17 are pg/ml, IL-6 are ng/dl, and IL-10 are pg/cl). Previous experience with this model has shown a progressive increases in IL-6 and IL-10 over a similar time period and a more persistent TNF signal.

EXAMPLE 2

Biocompatibility Index of the Adsorption Medium

The adsorption medium employed in Example 1 was subjected to the prescribed battery of tests under the biocompatibility index test protocol described above. The blood drawn from six individual healthy donors was subjected to the test protocol and the test results were averaged.

Figure 18A:
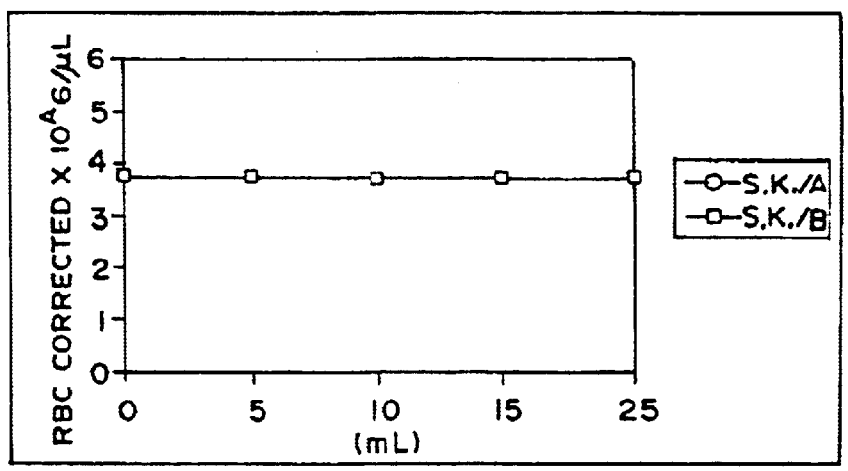
FIGS. 18 A, 18B, and 18C are graphs showing the variations in blood cell counts for red blood cells, white blood cells, and platelets, respectively, during passage of 25 ml of the blood through a treatment device containing an adsorbant medium useful for removing cytokines from the blood.
Figure 18B:
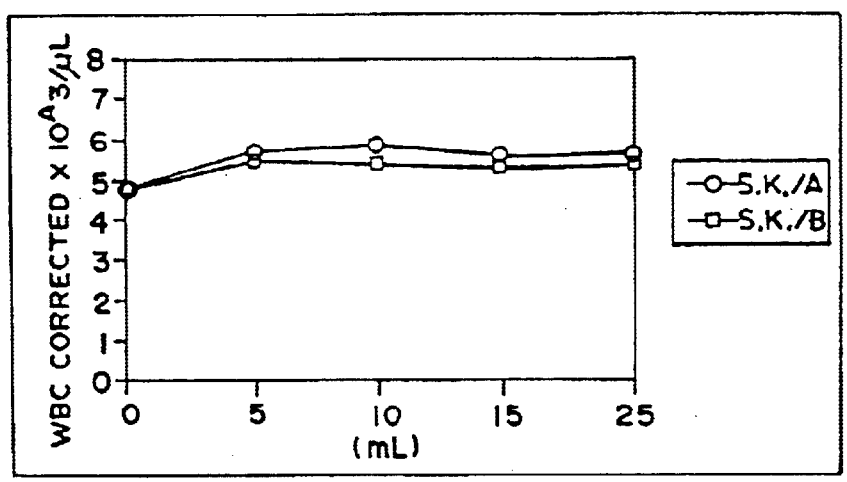
Figure 18C:
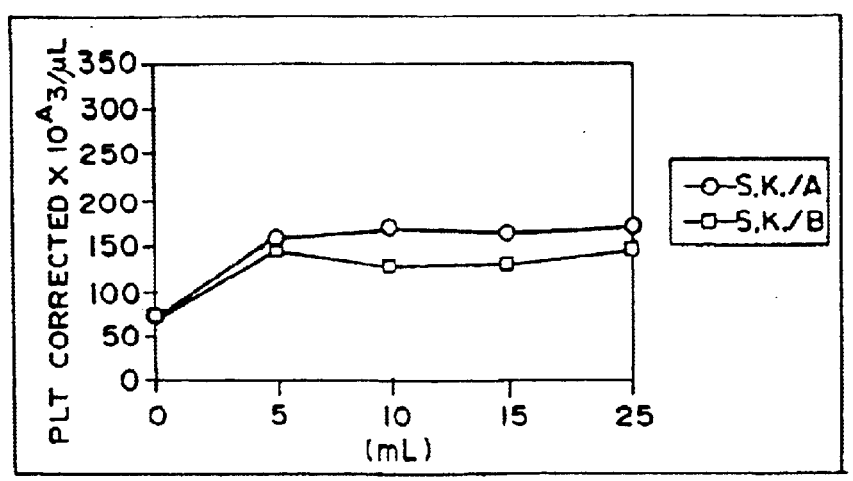

FIGS. 18 A, 18B, and 18C show the average variations in blood cell counts for red blood cells, white blood cells, and platelets, respectively, incrementally during passage of 25 ml of the blood through the treatment device containing the medium. With respect to red blood cells, white blood cells, and platelets, the maximum difference between the base line (line S.K./A) and the medium (line S.K./B) was less than 15%.

Figure 19:
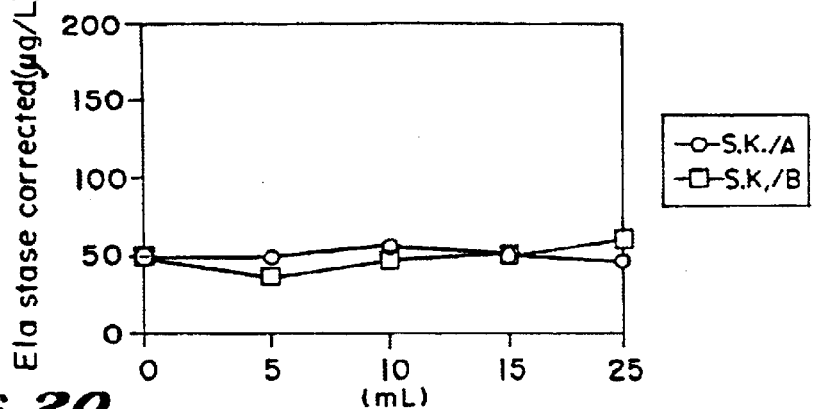
FIG. 19 is a graph showing the variations in PMN elastase concentrations (indicative of leukocyte activation) during passage of 25 ml of the blood through a treatment device containing an adsorbant medium useful for removing cytokines from the blood.

FIG. 19 shows the average variations in PMN elastase concentrations (indicative of leukocyte activation) incrementally during passage of 25 ml of the blood through the treatment device containing the medium. The maximum difference between the based line (line S.K./A) and the medium (line S.K./B) was less than 15%.

Figure 20:
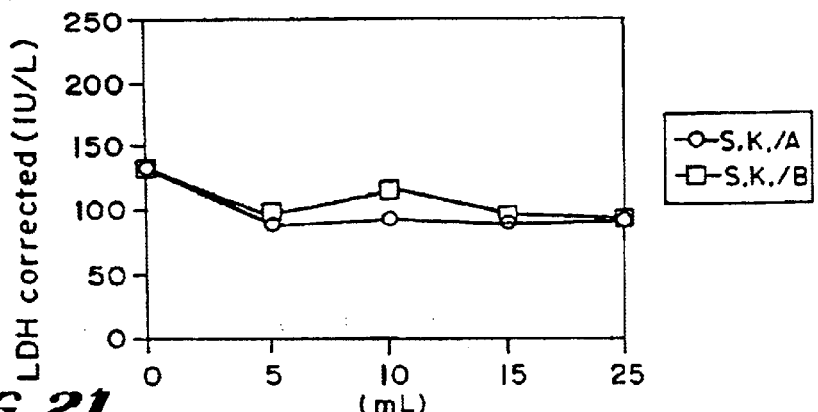
FIG. 20 is a graph showing the variations in LDH concentrations (indicative of hemolysis) during passage of 25 ml of the blood through a treatment device containing an adsorbant medium useful for removing cytokines from the blood.

FIG. 20 shows the average variations in LDH concentrations (indicative of hemolysis) incrementally during passage of 25 ml of the blood through the treatment device containing the medium. The maximum difference between the based line (line S.K./A) and the medium (line S.K./B) was less than 15%.

Figure 21:
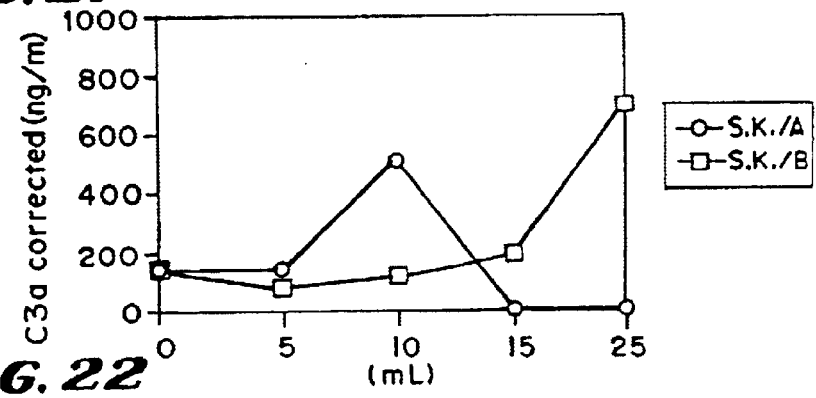
FIG. 21 is a graph showing the variations in C3a-desArg concentrations(indicative of complement activation) during passage of 25 ml of the blood through a treatment device containing an adsorbant medium useful for removing cytokines from the blood.

FIG. 21 shows the average variations in C3a-desArg concentrations(indicative of complement activation) incrementally during passage of 25 ml of the blood through the treatment device containing the medium. One donor experienced a rapid increase in the C3a-desArg level from 86 up to 822 µg/L due to clotting in the test system. The other five donors (who experienced no clotting in the test system) underwent more moderate increases, with a mean increase of from 113 to 392 µg/L. The maximum difference between the based line (line S.K./A) and the medium (line S.K./B) was greater than 25%.

Figure 22:
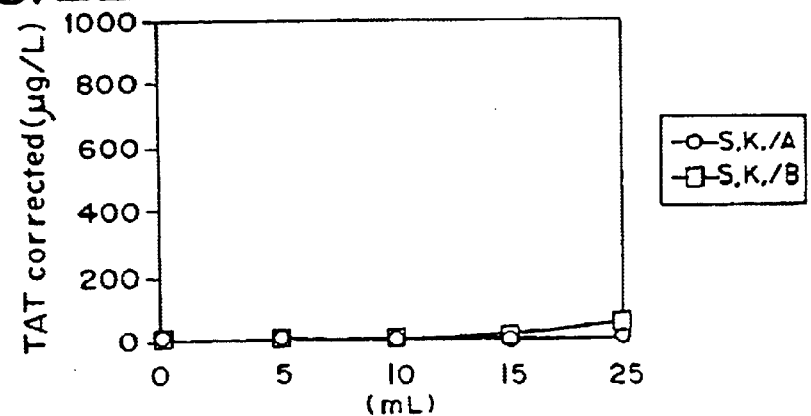
FIG. 22 is a graph showing the variations in TAT concentrations (indicative of coagulation) during passage of 25 ml of the blood through a treatment device containing an adsorbant medium useful for removing cytokines from the blood.

FIG. 22 shows the average variations in TAT concentrations (indicative of coagulation) incrementally during passage of 25 ml of the blood through the treatment device containing the medium. The maximum difference between the based line (line S.K./A) and the medium (line S.K./B) was less than 15%.

The following table lists the scoring the results for the indications as the dimensionless quantities 1, 2, and 3.

| Blood Indicator | Numeric Scores | | |
|---|---|---|---|
| | 1 (Signifying Most Desired Degree of Biocompatibility) | 2 (Signifying an Acceptable Degree of Biocompatibility) | 3 (Signifying a Least Desired Degree of Biocompatibility) |
| Loss /of White Blood Cells | 1 | | |
| Loss of Red Blood Cells | 1 | | |
| Loss of Platelets | 1 | | |
| PMN Elastase Concentration | 1 | | |
| LDH Concentration | 1 | | |
| C3a-desArg Concentration | | | 3 |
| TAT Concentration | 1 | | |

The Biocompatibility Index for the Medium is 9, which indicates the medium can contact the blood with no significant loss of blood cells, no significant hemolysis, no significant activation of luekocytes or monocytes, and, at most, only moderate complement activation, even with the use of heparin as the sole anticoagulant. Because such materials are not likely to induce the generation of cytokines, they are well suited for use to remove cytokines from the blood, blood products, or physiologic fluids.

Various features of the invention are set forth in the following claims.

We claim:

1. A system for treating an individual experiencing a chronic physiologic condition that is characterized by abnormal levels of cytokines or other species of pro-inflammatory or anti-inflammatory stimulators or mediators in the blood, the system comprising a material that removes cytokines or other species of pro-inflammatory or anti-inflammatory stimulators or mediators from blood by selective adsorption, and tubing for circulating the blood of the individual through the material, the tubing having a wall impregnated with the material.

2. A system according to claim 1 wherein the material comprises a polymeric material.

3. A system according to claim 2 wherein the polymeric material comprises particles prepared by polymerization or copolymerization of a monomer selected from a group consisting of styrene, ethylstyrene, α-methylstyrene, divinylbenzene, di isopropenyl benzene, trivinylbenzene, and alkyl methacrylate.

4. A system according to claim 2 wherein the polymeric material comprises particles formed from crosslinked polystyrene-type resins having a surface modified to minimize activation of blood complement system.

5. A system according to claim 2 wherein the polymeric material comprises particles formed from a porous hydrophobic divinylbenzene copolymer having a surface modified to include surface exposed functional groups selected from the group of polymers of 2-hydroxyethyl methacrylate, N-vinylpyrrolidine, N-vinylcaprolactame and N-acrylamide.

6. A system according to claim 2 wherein the polymeric material comprises particles formed by polymerization of aromatic divinyl compounds or their copolymerization with aromatic monovinyl compounds in the presence of porogens or mixtures of porogens with properties close to those of θ-solvents.

7. A system according to claim 1 wherein the material is characterized by a Biocompatibility Index of not greater than 14.

8. A system according to claim 7 wherein the Biocompatibility Index is not greater than 7.

9. A system according to claim 1 further including a source of an agent selected to be administered to the individual to treat the chronic physiologic condition.

10. A system according to claim 1 wherein the tubing includes an intravenous catheter.

11. A system according to claim 1 wherein the tubing includes an indwelling catheter.

12. A system according to claim 1 wherein the tubing is sized to be carried with the individual during ambulation.

13. A system for treating an individual experiencing trauma before onset of septic shock comprising a material that removes cytokines or other species of pro-inflammatory or anti-inflammatory stimulators or mediators from blood by selective adsorption, and tubing for circulating the blood of the individual through the material, the tubing having a wall impregnated with the material.

14. A system according to claim 13 wherein the material comprises a polymeric material.

15. A system according to claim 14 wherein the polymeric material comprises particles prepared by polymerization or copolymerization of a monomer selected from a group consisting of styrene, ethylstyrene, α-methylstyrene, divinylbenzene, di isopropenyl benzene, trivinylbenzene, and alkyl methacrylate.

16. A system according to claim 14 wherein the polymeric material comprises particles formed from crosslinked polystyrene-type resins having a surface modified to minimize activation of blood complement system.

17. A system according to claim 14 wherein the polymeric material comprises particles formed from a porous hydrophobic divinylbenzene copolymer having a surface modified to include surface exposed functional groups selected from the group of polymers of 2-hydroxyethyl methacrylate, N-vinylpyrrolidine, N-vinylcaprolactame and N-acrylamide.

18. A system according to claim 14 wherein the polymeric material comprises particles formed by polymerization of aromatic divinyl compounds or their copolymerization with aromatic monovinyl compounds in the presence of porogens or mixtures of porogens with properties close to those of θ-solvents.

19. A system according to claim 13 wherein the material is characterized by a Biocompatibility Index of not greater than 14.

20. A system according to claim 19 wherein the Biocompatibility Index is not greater than 7.

21. A system according to claim 13 further including a source of an agent selected to be administered to the individual to treat trauma.

22. A system according to claim 13 wherein the tubing includes an intravenous catheter.

23. A system according to claim 13 wherein the tubing includes an indwelling catheter.

24. A system according to claim 13 wherein the tubing is sized to be carried with the individual during ambulation.

* * * * *